United States Patent
Perrin et al.

(10) Patent No.: US 8,217,018 B2
(45) Date of Patent: Jul. 10, 2012

(54) REVERSIBLE SIRNA-BASED SILENCING OF MUTANT AND ENDOGENOUS WILD-TYPE HUNTINGTIN GENE AND ITS APPLICATION FOR THE TREATMENT OF HUNTINGTON'S DISEASE

(75) Inventors: Valérie Perrin, Lausanne (CH); Nicole Deglon, Le Plessis Robinson (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 216 days.

(21) Appl. No.: 12/665,137

(22) PCT Filed: Jun. 18, 2008

(86) PCT No.: PCT/IB2008/002603
§ 371 (c)(1),
(2), (4) Date: Jun. 9, 2010

(87) PCT Pub. No.: WO2009/007855
PCT Pub. Date: Jan. 15, 2009

(65) Prior Publication Data
US 2010/0299768 A1    Nov. 25, 2010

(30) Foreign Application Priority Data

Jun. 18, 2007 (EP) .................................... 07290751

(51) Int. Cl.
*A61K 31/70* (2006.01)
*C07H 21/02* (2006.01)
*C07H 21/04* (2006.01)
*C12N 5/00* (2006.01)
*C12Q 1/68* (2006.01)

(52) U.S. Cl. .................. 514/44 A; 536/23.1; 536/24.1; 536/24.5; 435/320.1; 435/375; 435/377

(58) Field of Classification Search .................. None
See application file for complete search history.

(56) References Cited

OTHER PUBLICATIONS

Denovan-Wright, et al., "RNAi: A Potential Therapy for the Dominantly Inherited Nucleotide Repeat Diseases", Gene Therapy, 13, pp. 525-531, 2006.
Wang, et al., "Clinico-Pathological Rescue of a Model Mouse of Huntington's Disease by siRNA", Neuroscience Research, 53, pp. 241-249, 2005.
Machida, et al., "rAAV-Mediated shRNA Ameliorated Neuropathology in Huntington Disease Model Mouse", Biochemical and Biophysical Research Communications, 343, pp. 190-197, 2006.
Rodriguez-Lebron, et al., "Intrastriatal rAAV-Mediated Delivery of Anti-Huntingtin shRNAs Induces Partial Reversal of Disease . . . ", Molecular Therapy, 12 pp. 618-633, 2005.
Harper, et al., "RNA Interference Improves Motor and Neuropathological Abnormalities . . . ", Procedings of the National Academy of Sciences of the USA, 102, pp. 5820-5825, 2005.

*Primary Examiner* — Sean McGarry
(74) *Attorney, Agent, or Firm* — Morgan, Lewis & Bockius LLP

(57) ABSTRACT

Isolated double-stranded short interfering nucleic acid molecules inhibiting the expression of endogenous wild-type and exogenous human mutant huntintin genes in cells of a non-human mammal which are expressing both said huntigtin genes, and their application for the treatment of Huntington's disease as well as to study Huntington's disease in rodent models.

20 Claims, 11 Drawing Sheets

Reversibility of siRNA silencing

Figure 1:
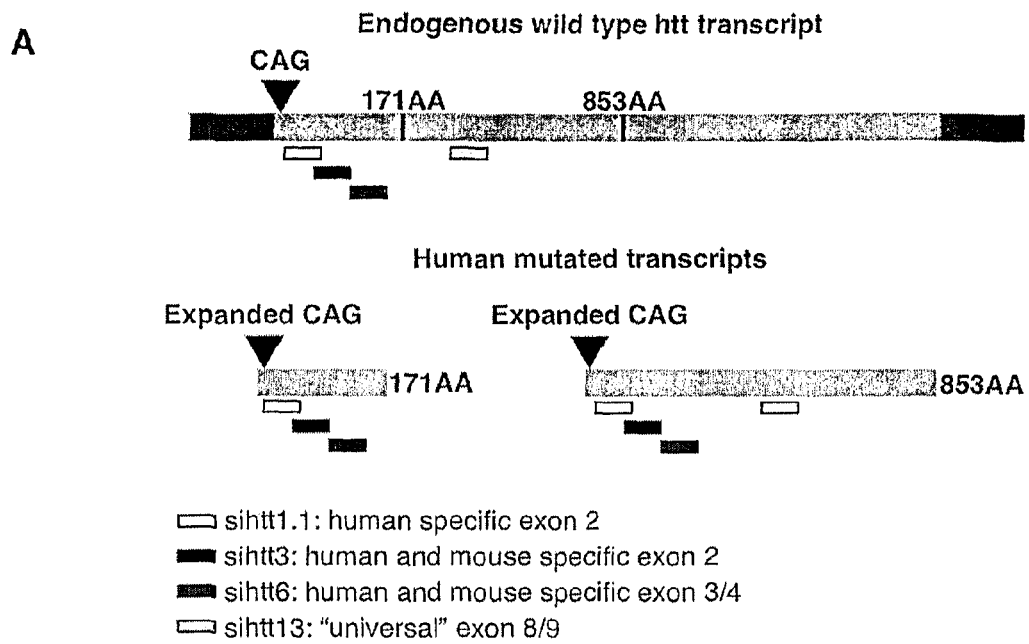
Figure 1:
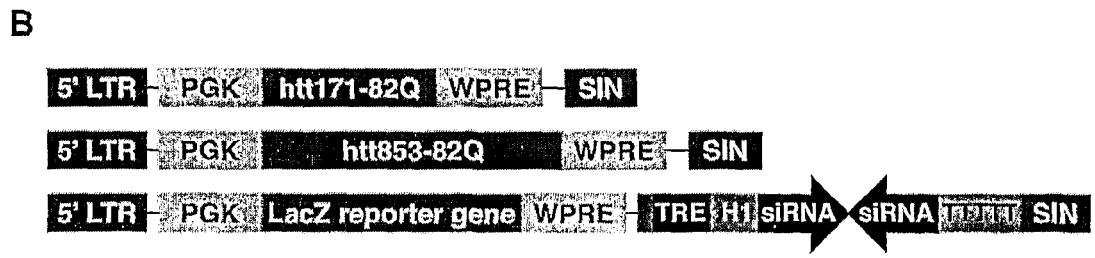
Figure 1:
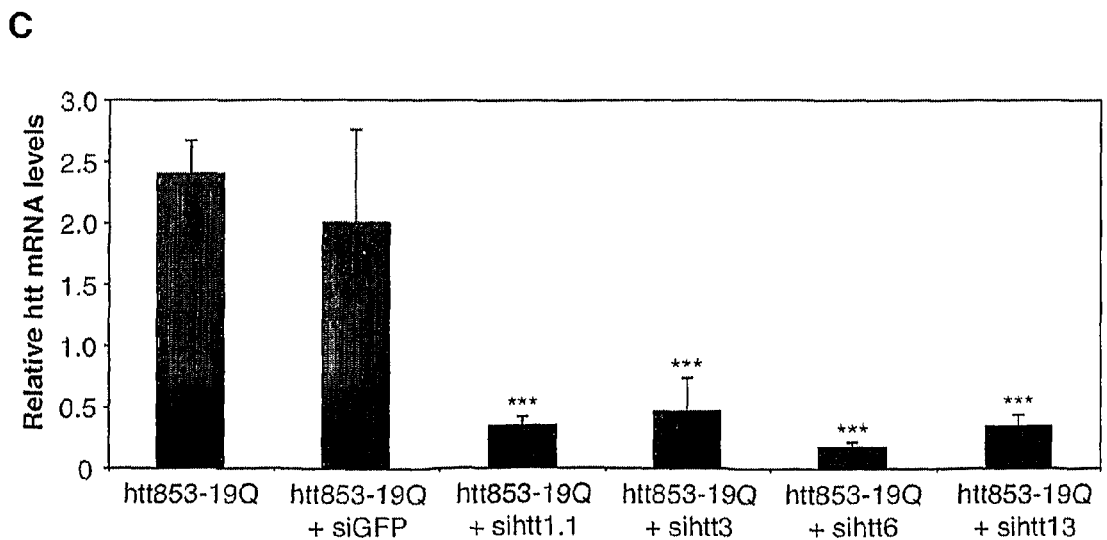

REVERSIBLE SIRNA-BASED SILENCING OF MUTANT AND ENDOGENOUS WILD-TYPE HUNTINGTIN GENE AND ITS APPLICATION FOR THE TREATMENT OF HUNTINGTON'S DISEASE

RELATED APPLICATIONS

The present application is a U.S. National Phase Application of International Application No. PCT/IB2008/002603 (filed Jun. 18, 2008), which claims priority to European Patent Application No. 07290751.2 (filed Jun. 18, 2007), all of which are hereby incorporated by reference in their entirety.

SEQUENCE LISTING SUBMISSION VIA EFS-WEB

A computer readable text file, entitled "045636-5125-SeqListing.txt," created on or about Dec. 15, 2009 with a file size of about 24 kb contains the sequence listing for this application and is hereby incorporated by reference in its entirety.

The present invention concerns short nucleic acid molecules which downregulate the expression of mutant and endogenous wild-type huntingtin gene by RNA interference and to their application for the treatment of Huntington's disease as well as to study Huntington's disease in rodent models.

Huntington's disease (HD) is a fatal autosomal dominant neurodegenerative disorder characterized by psychiatric manifestations, cognitive impairment, and involuntary choreiform movements (Vonsattel, J. P. and DiFiglia, M., *J. Neuropathol. Exp. Neurol.*, 1998, 57, 369-384). The mutation underlying Huntington's disease is an expansion of a CAG nucleotides repeat in the first exon of the huntingtin gene (htt), producing a mutant htt protein with an elongated polyglutamine (polyQ) tract in the N-terminal region of the htt protein. A CAG repeats number over 35 generally causes HD with age at onset correlating inversely with expansion length, a common characteristic to the polyglutamine repeat disorders (Group, T. H. s. D. C. R, *Cell*, 1993, 72, 971-983). The disease usually develops in midlife, but juvenile onset cases can occur with CAG repeat lengths over 60. Death typically occurs 10-15 years after symptom onset.

Despite the widespread expression of huntingtin (htt) throughout the brain, the affected region is limited to a subset of neurons in the striatum, the GABAergic spiny neurons. In a more advanced stage of the disorder, neuro-pathological changes occur in other brain regions, notably the cortex.

No cure or preventive treatments are available to slow disease onset or progression. However, studies performed on cellular and animal models of Huntington's disease have provided important clues about the molecular basis of mutant htt neurotoxicity. Impaired proteasomal degradation, altered gene transcription, protein misfolding, $Ca^{2+}$ abnormalities, defects in intracellular signaling, and activation of the apoptotic cascade have all been implicated in the pathogenesis of Huntington's disease (Petersen et al., *Exp. Neurol.*, 1999, 157, 1-18). These mechanisms may all represent potential therapeutic targets. Reducing the level of the causative agent, the mutant htt itself, however, represents the ultimate and most direct approach to block Huntington's disease pathogenesis.

RNAi is a form of post-transcriptional gene silencing mediated by short double stranded RNA (Brummelkamp et al., *Science*, 2002, 296, 550-553; Hannon, G. J., *Nature*, 2002, 418, 244-251; McManus, M. T. and Sharp, P. A., *Nat. Rev. Genet.*, 2002, 3, 737-747). Short double-stranded RNA molecules of 19-23 by (siRNA) induce degradation of cognate homologous mRNA via the RNA-induced silencing complex (RISC). Conversion of small hairpin RNA (shRNA), synthesized from a DNA template by RNA polymerase II or III promoters into small interfering RNA (siRNA), is achieved by the cellular ribonuclease III, Dicer (Dykxhoorn et al., *Nat. Rev. Mol. Cell. Biol.*, 2003, 4, 457-467; Hammond, S. M., *FEBS Lett.*, 2005, 579, 5822-5829; Harmon, G. J. and Rossi, J. J., *Nature*, 2004, 431, 371-378). To ensure a continuous and long-term expression of siRNA in the central nervous system (CNS) and overcome delivery issues associated with the presence of the blood-brain barrier, gene transfer approaches have been investigated. Expression systems for the stable expression of siRNAs in mammalian cells have been developed (Brummelkamp et al., *Science*, 2002, 296, 550-553; Sui et al., *P.N.A.S.*, 2002, 99, 5515-5520; Barton et al., *P.N.A.S.*, 2002, 99, 14943-14945). RNA pol II or RNA pol III promoters (U6 and H1) have been used to express shRNA or siRNAs in viral vectors (Barton et al., *P.N.A.S.*, 2002, 99, 14943-14945; Devroe, E. and Silver, P. A., *BMC Biotechnol.*, 2002, 2, 15-; Shen et al., Hum. Gene Ther., 2002, 13, 2197-2201). Lentiviral vectors encoding siRNAs were shown to provide long-term gene silencing in mammalian cells, including neurons (Abbas et al., *Hum. Gene Ther.*, 2002, 13, 2197-2201; Rubinson et al., *Nat. Genet.*, 2003, 33, 401-406; Stewart et al., *RNA*, 2003, 9, 493-501; Tiscornia et al., *P.N.A.S.*, 2003, 100, 1844-1848; Bridge et al., *Nat. Genet.*, 2003, 34, 263-264; Matta et al., *Cancer Biol. Ther.*, 2003, 2, 206-210; Krichevsky, A. M., and Kosik, K. S., *P.N.A.S.*, 2002, 99, 11926-11929). The possibility of designing and integrating siRNA in expression vectors makes this therapeutic approach particularly attractive. The proof of principle for the dominant diseases spinocerebellar ataxia type 1, 3 and Huntington's disease has been demonstrated (Sah, D. W. Y., Life Sciences, 2006; Denovan-Wright, E. M. and Davidson, B. L., *Gene Therapy*, 20 Oct. 2005, 1-7; Chen et al., *Biochem. Biophys. Res. Commun.*, 2005, 329, 646-652; Harper et al., *Proc. Nat. Acad. Sci. USA*, 2005, 102, 5820-5825; Huang, B. and Kochanek, S., *Hum. Gene Ther.*, 2005, 16, 618-626; Machida et al., *Biochem. Biophys. Res. Commun.*, 2006, 343, 190-197; Omi et al., *Biochem. Biophys. Res. Commun.*, 2005, 338, 1229-1235; Rodriguez-Lebron et al., *Mol. Ther.*, 2005, 12, 618-633; Wang et al., *Neurosci. Res.*, 2005, 53, 241-219; Xia et al., *Nat. Med.*, 2004, 10, 816-820; Xia et al., *Nat. Biotechnol.*, 2002, 20, 1006-1010; International PCT Applications WO 2006/031267, WO 2005/116212, WO 2005/105995).

Despite these encouraging results, several issues still need to be addressed before considering clinical applications of siRNA for polyQ disorders, and in particular Huntington's disease.

The first concern is the possible necessity for allele-specific silencing in order to preserve expression of wild-type htt in affected patients. To date, all studies performed in vitro or in transgenic mice models of polyQ disorders, utilized siRNAs specifically targeting the human mutant transcript not the endogenous mouse wild-type htt allele. In Huntington's disease, the dominant gain-of-function effect of mutant htt has been demonstrated. However, studies suggest that wild-type htt also plays a role in the survival of adult neurons and that loss-of-function may also contribute to the disease process (Cattaneo, E., *News Physiol. Sci.*, 2003, 18, 34-37). Interestingly, a 50% reduction of wild-type htt expression (one functional htt allele) does not affect the survival of neurons in mice (Duyao et al., Science, 1995, 269, 407-410; Zeithin et al., Nat. Genet., 1995, 11, 155-163) and human (Ambrose et al., *Somat. Cell. Mol. Genet.*, 1994, 20, 27-38; Persichetti et al., *Neurobiol. Dis.*, 1996, 3, 183-190). However, conditional gene inactivation which results in 84% reduction in htt protein in adult mice, triggers neurodegeneration of striatal and cortical neurons (Dragatsis et al., *Nat. Genet.*, 2000, 26, 300-306). The question of whether the coincident silencing of the normal endogenous wild-type htt would have deleterious effects has not previously been addressed and represents a critical issue toward clinical development. Thus, it is important to determine whether a long-term reduction of wild-type htt expression could be tolerated in adult brains. A global htt silencing approach would avoid the cost of developing individual therapy and genetic testing of Huntington's disease patients while siRNA targeting the mutant htt allele selectively represents the safest strategy.

A second concern is the necessity to have a potent expression system to ensure long-term and robust silencing of mutant htt mRNA in large brain areas. Studies in Huntington's disease transgenic models should provide information on behavioral and functional recovery associated with delivery of siRNA targeting htt (sihtt). Whether a local and partial inactivation of htt in the striatum will be sufficient to delay disease progression and improve the cognitive declines and motor disturbances in Huntington's disease patients or whether additional brain structures should be considered remains to be established. An encouraging result is provided by the study of Xia et al. (*Nature Biotechnology*, 2002, 20, 1006-1010) who showed that, in SCA1 transgenic mice, disease progression was mitigated with a partial infection of the cerebellum with an AAV-siRNA vector targeting ataxin.

Finally, in a chronic neurodegenerative disease like Huntington's disease, pharmacological regulation of siRNA will be particularly important as a safety strategy. It would be preferable to shut off siRNA expression if needed, to control potential side effects resulting from long-term and continuous expression of siRNA targeting htt in the brain. In addition, conditional expression of siRNA will be particularly important to further dissect the kinetic and long-term effects of siRNA in the brain. Pharmacologically controlled promoters are amongst the most potent tools to control gene expression (Gossen, M. and Bujard, H., *Proc. Natl. Acad. Sci. USA*, 1992, 89, 5547-5551; Gossen et al., *Science*, 1995, 268, 1766-1769). Among these, the tetracycline-regulated system is particularly suitable for the CNS applications because doxycycline, a tetracycline analog, crosses the blood-brain barrier (Barza et al., *Antimicrob. Agents Chemother.*, 1975, 8, 713-720).

To investigate the impact of the silencing of endogenous wild-type htt in rodent models, the inventors have designed small interfering RNAs (shRNA) with various species specificities. Doxycycline-regulated lentiviral vectors allowing regulated expression of shRNAs specifically targeting endogenous wild-type and/or human mutant htt mRNA (sihtt) were produced to control sihtt treatment and reversibility of the system. Long-term expression of species specific (human and/or rat and/or mouse) shRNAs in the striatum of rodent models of Huntington's disease was used to evaluate therapeutic efficacy and enabled the inventors to test a strategy mimicking a general silencing of htt or a specific downregulation of the disease allele.

At least three shRNA (sihtt1.1 (exon 2), sihtt3 (exon 2) and sihtt6 (exon 4)) tested dramatically reduced Huntington's disease pathology, with over 85% DARPP-32 expression recovery and a nearly complete clearance of htt inclusions in rats and mouse models. The use of lentiviral vectors leading to high transduction efficiency in the CNS and the robust transgene expression levels obtained by the integration of an H1-shRNA expression cassette in the 3'LTR of the transfer vector, contribute to the effectiveness of the approach. In addition, it was demonstrated that this approach resulted in sustained expression of sihtt up to 9 months; this type of long-term delivery will be essential for the successful treatment of chronic neurodegenerative disease like HD.

A proof of concept of sihtt conditional expression in the brain was shown with the TetR-KRAB transrepressor and the H1 polymerase III promoter, to achieve doxycycline-regulated expression of htt-targeted siRNAs, in rodent models of Huntington's disease. A tight regulation of sihtt expression was obtained despite the fact that the system depended on three plasmids. This system was used to evaluate the reversibility of Huntington's disease pathology and therefore provides information on the window for therapeutic intervention in Huntington's disease. The results obtained in −DOX/+DOX animals, demonstrated that initiating sihtt treatment after the onset of Huntington's disease symptoms is still effective in diminishing polyQ toxicity, as assessed by a significantly reduced loss of expression of the striatal marker, DARPP-32 and a partial clearance of htt inclusions.

The in vivo studies addressing the question of the impact of global silencing, demonstrated that a reduction of normal htt expression in adult striatal neurons to 25-35% of normal levels is well tolerated for up to 9 months. The expression of siRNAs with various species specificities in the striatum of mice and rats induced a downregulation of endogenous htt in mice and rats in accordance with the predicted selectivity and the downregulation of endogenous and/or mutant htt in rodent was not associated with a decreased therapeutic efficacy or increased striatal vulnerability. No signs of toxicity, degeneration of the striatum or loss of expression of striatal markers or the LacZ reporter gene present in the siRNA vector were observed after long-term expression of the siRNAs in rodent brains. The microarray analysis indicated that several pathways associated with known function of htt are altered when endogenous wild-type htt is silenced in adult mice. Nonetheless these results suggest that a local (striatum), long-term and partial inactivation of endogenous htt in adult mice is feasible. The residual level of htt transcript in the striatum of treated animals might be sufficient to maintain biological functions contrary to HD conditional knockout mice (Dragatsis et al., *Nat. Genet.*, 2000, 26, 300-306) where the complete inactivation of htt gene in a large proportion of neurons just after embryonic development was associated with a drastic reduction in htt expression in the entire brain and early death.

Altogether, these results demonstrated that: (i) silencing of mutant htt dramatically reduced the Huntington's disease-like neuropathology in rodents, (ii) sihtt-treatment initiated after the onset of Huntington's disease pathology is still efficacious and reduces Huntington's disease neuropathology in rodents, (iii) both exogenous mutant htt and endogenous wilt-type transcript are efficiently silenced in vivo, (iv) the silencing of endogenous htt significantly causes transcriptomic changes in molecular pathways associated with known htt functions, (v) this partial inactivation of endogenous wild-type htt is not exacerbating Huntington's disease pathology, and (vi) this silencing does not alter GABAergic neuron survival or change the therapeutic efficacy of sihtt after short- and mid-range treatments and at levels of 65-75% silencing.

These data established the efficacy of lentiviral-mediated silencing for HD and showed for the first time the long-term impact of a partial inactivation of wild-type htt.

Taken together, these results establish the potential of siRNAs as therapeutic tools to counteract Huntington's disease and suggest that the coincident silencing of the wild-type and mutant htt might be considered as a relevant and viable approach for Huntington's disease patients.

Therefore, the invention provides an isolated double-stranded short interfering nucleic acid molecule comprising complementary sense and antisense regions, wherein:

the antisense region has 15 to no more than 19 contiguous nucleotides that are complementary to a human htt transcript, said nucleotides being encoded by a sequence selected from the group consisting of SEQ ID NO: 1 to 3, the sense and antisense regions have at least 15 contiguous nucleotides that are complementary to each other and form a duplex, and said double-stranded short interfering nucleic acid molecule inhibits the expression of endogenous wild-type and exogenous human mutant htt genes in cells of a non-human mammal which are expressing both said htt genes.

Definitions

"short nucleic acid molecule" refers to a nucleic acid molecule no more than 100 nucleotides in length, preferably no more than 80 nucleotides in length, and most preferably, no more than 50 nucleotides in length.

"interfering nucleic acid molecule or siNA molecule" refers to a duplex of short nucleic acid molecule capable of inducing the process of sequence specific post-transcriptional gene silencing, as first described by Elbashir et al., Nature 2001, 411, 494- and in the International PCT Application WO 01/75164, upon introduction of said siNA in cells. A siNA is targeted to a gene of interest in that the nucleotide sequence of the duplex portion of the siNA molecule is complementary to a nucleotide sequence of a targeted gene.

"duplex" refers to the structure formed by the complementary pairing between two regions of a nucleic acid molecule.

"nucleic acid" refers to deoxyribonucleic acid (DNA), ribonucleic acid (RNA) and mixed nucleic acid including natural nucleotides containing a sugar, a phosphate and a base (adenine, cytosine, guanine, thymine or uracil), known analogs of natural nucleotides or nucleotides that are modified at the sugar, phosphate, and/or base moiety.

"nucleotide encoded by a sequence SEQ ID NO: X" refers to a deoxyribonucleotide of the DNA sequence SEQ ID NO: X or a ribonucleotide (a, g, c, u) corresponding to the (a, g, c, t) deoxyribonucleotide of the DNA sequence SEQ ID NO: X.

"complementary" refers to the ability of a nucleic acid to form hydrogen bond(s) by either traditional Watson-Crick base-pairing or other non-traditional type base-pairing. In reference to the nucleic acid molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well-known in the art (see, e.g., Turner et al., 1987, *CSH Symp. Quant. Biol.*, 1987, LII, pp 123-133, Frier et al., *P.N.A.S.*, 1986, 83, 9373-9377; Turner at al., *J. Am. Chem. Soc.*, 1987, 109, 3783-3785). A percent complementarity indicates the percentage of contiguous residues in a nucleic acid molecule that can form hydrogen bonds (e.g., Watson-Crick base-pairing) with a second nucleic acid sequence (e.g., 5, 6, 7, 8, 9, or nucleotides out of a total of 10 nucleotides, in the first oligonucleotide being base-paired to a second nucleic acid sequence having 10 nucleotides represents 50%, 60%, 70%, 80%, 90% and 100% complementarity, respectively). "Perfectly complementary" means that all the contiguous residues of a nucleic acid sequence will hydrogen bond with the same number of contiguous residues in a second nucleic acid sequence.

"transcript" refers to the product resulting from RNA polymerase catalyzed transcription of a DNA sequence; it includes the primary transcript, the mature RNA and the mRNA.

"endogenous gene" refers to a native gene in its natural location in the genome of an host organism/cell.

"exogenous gene" refers to a gene that originates from a source foreign to the particular host organism/cell, "wild-type" refers to the normal gene found in nature.

"htt gene" or "huntingtin gene" refers to the gene encoding the huntingtin protein (htt) that is associated with the Huntington's disease (HD). The sequence of the human htt gene corresponds to the accession number NC__000004 in the NCBI data base. The sequence of the htt gene of other mammals is also available in the sequence data bases.

"mutant htt gene" or "disease htt gene" refers to an htt gene having an expansion of 35 or more CAG repeats in the first exon and producing a mutant htt protein with an elongated polyglutamine (polyQ) tract that causes Huntington's disease.

"vector" refers to a nucleic acid molecule capable of transporting another nucleic acid to which it has been linked.

The siNA molecule according to the invention targets one region of the human htt transcript corresponding to positions 442 to 460 (exon 2), 619 to 637 (exon 4) or 1207 to 1225 (exons 8-9), by reference to the human htt mRNA sequence NCBI accession number NM__002111 or SEQ ID NO: 11.

TABLE I siNA targeting the human htt gene

| Target positions | exon | Sense strand sequence | Identification number | Antisense strand sequence | Identification number |
|---|---|---|---|---|---|
| 442-460 | 2 | agaccgtgtgaatcattgt | SEQ ID NO: 4 | tctggcacacttagtaaca | SEQ ID NO: 1 |
| 619-637 | 4 | agctttgatggattctaat | SEQ ID NO: 5 | tcgaaactacctaagatta | SEQ ID NO: 2 |
| 1207-1225 | 8-9 | gcagcttgtccaggtttat | SEQ ID NO: 6 | cgtcgaacaggtccaaata | SEQ ID NO: 3 |

The siNA molecule according to the invention decreases the level of both wild-type and mutant human htt mRNA and protein, by at least 40%, preferably at least 60%, more preferably at least 80% in a human cell expressing both htt mRNAs and proteins. In addition, the siNA molecule decreases the level of wild-type endogenous and mutant human htt mRNA and protein, by at least 40%, preferably at least 60%, more preferably at least 80%, in at least one non-human mammalian cell expressing both htt mRNAs and proteins. The human cell may be a cell carrying a mutant human htt allele carrying 35 or more CAG repeats in exon 1 or a cell transformed by a DNA construct comprising a mutant human gene or a N-terminal fragment thereof which are well known in the art. For example, the DNA construct encodes the first 171 amino acids of htt protein with 82 CAG repeat. (N171-82Q or htt171-82Q). The non-human mammalian cell is a cell transformed by a DNA construct comprising a mutant human gene or a N-terminal fragment thereof, as defined above. The cell may be from a rodent, preferably from rat or mice. For example the cell is from a transgenic mice or a transgenic rat.

The siNA targeting exon 2 and the siNA targeting exon 4 are human and murine specific; they down-regulate the endogenous human and murine htt genes and the mutant human htt gene but not the endogenous rat htt gene.

The siNA targeting exon 8-9 is human, murine and rat specific; this siNA down-regulates the endogenous human, murine and rat htt genes and the mutant human htt gene.

The silencing of both endogenous wild-type and human mutant htt genes is assessed at the RNA or protein level, by methods well-known in the art, for example by real time quantitative RT-PCR, FACS or immunohistological analyses.

According to one embodiment of the invention, the sense region of the siNA molecule comprises at least 15 contiguous nucleotides that are encoded by a sequence selected from the group consisting of SEQ ID NO: 4 to 6.

According to another embodiment of the invention, the siNA molecule is assembled from two separate oligonucleotides, each of 15 to about 30 (e.g. about 15, 16, 17, 18, 19, 20, 21, 22, 23, 24, 25, 26, 27, 28, 29, or 30) nucleotides, where the first strand comprises the sense region (sense strand) and the second strand comprises the antisense region (antisense strand) and said first and second strand form a (symmetric or asymmetric) duplex or double-stranded structure of at least 15 base pairs, preferably of 19 base pairs. For example, the antisense strand comprises or consists of the sequence SEQ ID NO: 1 to 3 and the sense strand comprises or consists of the sequence SEQ ID NO: 4 to 6, respectively.

According to another embodiment of the invention, the complementary sense and antisense regions of the siNA molecule are connected by means of nucleic acid based or non-nucleic acid based linker(s). A non-nucleotide linker comprises abasic nucleotides, aptamers, polyether, polyamine, polyamide, peptide, carbohydrate, lipid, polyhydrocarbon, or other polymeric compounds. For example, the siNA molecule is assembled from a single (linear or circular) oligonucleotide of 31 to about 50 (e.g. about 31, 32, 33, 34, 35, 36, 37, 38, 39, 40, 41, 42, 43, 44, 45, 46, 47, 48, 49 or 50) nucleotides where the sense and antisense regions are operably linked by means of polynucleotide loop(s) to form a structure comprising a duplex structure and one or more loop structures. The siNA comprises advantageously one duplex structure and one loop structure to form a symmetric or asymmetric hairpin secondary structure (shNA). In these structures, the duplex is of at least 15 base pairs, preferably of 19 base pairs. The loop(s) contains 4 to 10 nucleotides, such as 4, 5 or 6 nucleotides. The loop(s) is advantageously encoded by SEQ ID NO: 7 (5'-ttcaagaga-3'). For example, the siNA is a shNA encoded by a sequence selected from the group consisting of SEQ ID NO: 8 to 10.

TABLE II shNA targeting the human htt gene

| Sequence* | Identification number |
|---|---|
| agaccgtgtgaatcattgtttcaagagaacaatga ttcacacggtct | SEQ ID NO: 8 |
| agctttgatggattctaatttcaagagaattagaa tccatcaaagct | SEQ ID NO: 9 |
| gcagcttgtccaggtttatttcaagagaataaacc tggacaagctgc | SEQ ID NO: 10 |

*the sequence of the loop of the hairpin structure are in bold characters.

According to another embodiment of the invention, the siNA molecule comprises overhanging nucleotide(s) at one or both end(s), preferably, 1 to about 3 (e.g. about 1, 2, or 3) overhanging nucleotides. The overhanging nucleotides which are advantageously at the 3' end(s) are preferably 2'-deoxynucleotide(s), preferably 2'deoxypyrimidine(s), such as a 2'-deoxythymidine(s). For example, the siNA molecule consists of a first and a second strand, each of 21 nucleotides, where the first and the second strand form a 19 base pairs duplex with tt overhangs at both 3' ends of the duplex. Alternatively, the siNA molecule consists of a shNA having a 19 by duplex and a 4 to 10 nucleotides loop strand, where the 3' end of the hairpin structure has a tt overhang.

According to another embodiment of the invention, the siNA molecule comprises blunt end(s), where both ends are blunt. For example, the siNA molecule consists of a first and a second strand, each of 19 nucleotides, wherein the first and the second strand form a 19 base pairs duplex where both ends of the duplex are blunt. Alternatively, the siNA molecule consists of a shNA having a 19 by duplex and a 4 to 10 nucleotides loop strand, where both ends of the hairpin structure are blunt.

According to another embodiment of the invention, the siNA molecule comprises bulges, loops or wobble base pairs to modulate the activity of the siNA molecule to mediate RNA interference.

According to another embodiment of the invention, the siNA molecule comprises ribonucleotide(s) (2'-OH nucleotides) at about 5% to 100% of the nucleotide positions (e.g., about 5%, 10%, 15%, 20%, 25%, 30%, 35%, 40%, 45%, 50%, 55%, 60%, 65%, 70%, 75%, 80%, 85%, 90%, 95% or 100% of the nucleotide positions). For example, the siNA is an RNA molecule (siRNA molecule). Alternatively, the siNA molecule is mixed nucleic acid molecule comprising both deoxynucleotides and ribonucleotides.

According to another embodiment of the invention, the siNA molecule includes one or more modifications which increase resistance to nuclease degradation in vivo and/or improve cellular uptake. The siNA may include nucleotides which are modified at the sugar, phosphate, and/or base moiety, and/or modifications of the 5' or 3' end(s), or the internucleotidic linkage. For example, the siNA molecule comprises one or more modified pyrimidine and/or purine nucleotides, preferably on each strand of the double-stranded siNA. More preferably, said modified nucleotides are selected from the group consisting of: 2'-O-methylnucleotides, 2'-O-methoxyethylnucleotides, deoxynucleotides, such as 2'-deoxynucleotides and 2'-deoxy-2'-fluoronucleotides, universal base nucleotides, acyclic nucleotides and 5-C-methyl nucleotides. An siNA molecule of the invention can generally comprise about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given siNA molecule will depend on the total number of nucleotides present in the siNA molecule. The percent modification can be based upon the total number of nucleotides present in the sense strand, antisense strand or both the sense and the antisense strands.

According to another embodiment of the invention, the strand of the siNA that comprises the sense region (sense strand) includes a terminal cap moiety at the 5'-end, the 3'-end, or both the 5' and 3' ends of the strand, preferably a deoxy abasic moiety or glyceryl moiety.

According to another embodiment of the invention, the strand of the siNA that comprises the antisense region (antisense strand) includes a phosphate group at the 5'-end.

According to another embodiment of the invention, the siNA molecule comprises at least one modified internucleotidic linkage, such as a phosphorothioate linkage.

The invention encompasses the synthetic, semi-synthetic or recombinant siNAs as defined above.

The siNA molecules according to the invention may be produced by chemical synthesis by using well-known oligonucleotides synthesis methods which make use of common nucleic acid protecting and coupling groups, such as dimethoxytrityl at the 5'-end and phosphoramidites, at the 3' end. The nucleic acid molecules of the present invention can be modified to enhance stability by modification with nuclease resistant groups, for example 2'-amino, 2'-C-allyl, 2'-fluoro, 2'-O-methyl, 2'-H (for a review see Usman and Cedergren, *TIBS*, 1992, 17, 34 and Usman et al., *Nucleic Acids Symp. Ser.*, 1994, 31, 163). Examples of such modified oligonucleotides include with no limitation: 2' F-CTP, 2' F-UTP, 2' NH$_2$-CTP, 2' NH$_2$-UTP, 2' N$_3$-CTP, 2-thio CTP, 2-thio UTP, 4-thio UTP, 5-iodo CTP, 5-iodo UTP, 5-bromo UTP, 2-chloro ATP, Adenosine 5'-(1-thiotriphosphate), Cytidine 5'-(1-thiotriphosphate), Guanosine-5'-(1-thiotriphosphate), Uridine-5'-(1-thiotriphosphate), Pseudo-UTP, 5-(3-aminoallyl)-UTP and 5-(3-aminoallyl)-dUTP. siNA constructs can be purified by gel electrophoresis using general methods or can be purified by high pressure liquid chromatography (HPLC) and re-suspended in water.

The chemically-synthesized siNA molecule according to the invention may be assembled from two distinct oligonucleotides which are synthesized separately. Alternatively, both strands of the siNA molecule may be synthesized in tandem using a cleavable linker, for example a succinyl-based linker.

Alternatively, the siNA molecules of the invention may be expressed (in vitro or in vivo) from transcription units inserted into DNA or RNA vectors known to those skilled in the art and commercially available.

The invention provides also a transcription unit comprising: a transcription initiation region, a transcription termination region, and a nucleic acid sequence encoding a least one siNA molecule according to the present invention, wherein said nucleic acid sequence is operably linked to said initiation and termination regions in a manner that allows expression and/or delivery of the siNA molecule in a host cell, for example a target cell (neuron).

The nucleic acid sequence may encode one or both strands of the siNA molecule, or a single self-complementary strand that self-hybridizes into an siNA duplex.

The transcription initiation region may be from a promoter for a eukaryotic RNA polymerase II or III (pol II or III) including viral promoters (SV40, CMV, RSV, adenovirus), since transcripts from these promoters are expressed at high levels in all cells. Alternatively, prokaryotic RNA polymerase promoters may be used, providing that prokaryotic RNA polymerase enzyme is expressed in the appropriate cells. Preferred promoters are mouse U6 RNA, human H1 RNA and adenovirus VA RNA, which are useful in generating high concentrations of desired siNA in cells.

In addition, the promoter may be constitutive, regulatable (conditional expression) or tissue specific.

Preferred promoters are regulatable promoters, such as for example tetracycline-regulated promoters (Gossen, M. and Bujard, H., *Proc. Natl. Acad. Sci. USA*, 1992, 89, 5547-5551; Gossen et al., *Science*, 1995, 268, 1766-1769; Deuschle et al., *Mol. Cell. Biol.*, 1995, 15, 1907-1914). More preferably, the promoter is a doxycycline-regulated promoter which is particularly suitable for the CNS applications because doxycycline, a tetracycline analog, is crossing the blood-brain barrier.

The transcription termination region is recognized by a eukaryotic RNA polymerase, preferably pol II or pol III, for example, it is a TTTTT sequence.

The invention concerns also an expression vector comprising a nucleic acid encoding at least one siNA molecule of the instant invention. The expression vector may encode one or both strands of the siNA molecule, or a single self-complementary strand that self-hybridizes into a siNA duplex. The nucleic acid encoding the siNA molecule of the instant invention is preferably inserted in a transcription unit as defined above. The expression vector may also encode a factor that is essential for conditional expression of the siNA, such as for example an activator/repressor.

Large numbers of DNA or RNA vectors suitable for siNA molecule expression are known to those of skill in the art and commercially available (Déglon et al., *J. Gene Med.*, 2005, 7, 530-539). The recombinant vectors can be DNA plasmids or viral vectors. SiNA expressing viral vectors can be constructed based on, but not limited to, adeno-associated virus, retrovirus, lentivirus, adenovirus or alphavirus. The recombinant vectors capable of expressing the siNA molecules can be delivered in vivo, and persist in target cells. Alternatively, viral vectors can be used to provide transient expression of siNA molecules.

Lentivirus vectors (Naldini et al., *Science*, 1996, 272, 263-267; Naldini et al., *P.N.A.S.*, 1996, 93, 11382-11388) are one example of preferred vectors since they persist in target cells and thus provide long-term expression of the siNA and consequently long-term gene-silencing in mammalian cells, including neurons. More preferred vectors are multiply attenuated lentiviral (Zufferey et al., *Nat. Biotechnol.*, 1997, 15, 871-875) and replication-defective lentiviral vectors that have been modified to increase transgene expression (SIN-W and SIN.cPPT-W vectors; Dull et al., *J. Virol.*, 1998, 72, 8463-8471; Zufferey et al., *J. Virol.*, 1999, 73, 2886-2892; Follenzi et al., *Nat. Genet.*, 2000, 25, 217-222; Déglon et al., *Human Gene Therapy*, 2000, 11, 179-190; de Almeida et al., *J. Neurosci.*, 2002, 22, 3473-3483). Tetracycline regulated lentiviral vectors are described for example in Wiznerowicz, M. and Trono, D., *J. Virol.*, 2003, 77, 8957-8961; Régulier et al., Human Mol. Genetics, 2003, 12, 2827-2836; Régulier et al., *Human Gene Therapy*, 2002, 13, 1981-1990.

The invention provides also a eukaryotic or prokaryotic host cell which is modified by a vector as defined above.

The invention concerns also the use of at least one siNA molecule or vector as defined above, to study Huntington's disease in a rodent model, rat or mouse for example.

Rodent model's of Huntington's disease are well-known in the art (Regulier et al., *Methods in Molecular Biology,* 2007, 277, 199-213; Bates G. P. and Gonitel R., *Mol. Biotechnol.,* 2006, 32, 147-158; Azzouz et al., *J. Gene Med.,* 2004, 6, 951-962; Déglon, N. and Hantraye, P., *J. Gene Med.,* 2005, 7, 530-539).

The siNA targeting exon 2 or exon 4 (human and mouse specific) or the siNA targeting exon 8-9 (human, mouse and rat specific) are used in mouse model of HD to study the effect of endogenous htt gene silencing on neuron survival, disease progression and siNA treatment efficacy.

The siNA targeting exon 8-9 (human, mouse and rat specific) is also used in rat model of HD to study the effect of endogenous htt gene silencing on neuron survival, disease progression and siNA treatment efficacy.

In addition since exon 8-9 is not present in the shorter versions of the mutant human htt gene (htt171-82Q), siNA targeting exon 8-9 is used as control to assess the silencing of the sole endogenous htt gene on neuron survival and disease progression in mouse or rat models that uses the human htt171-82Q gene as disease htt gene.

In these animal studies, human specific siNAs which are well-known in the art may be used, as control, to assess the silencing of the sole human mutant htt gene. Human siNA targeting exon 2 that can improve the symptoms of HD in vivo in a rodent model, have been described previously (International PCT Application WO 2006/031267 and Harper et al., *P.N.A.S.,* 2005, 102, 5820-5825). Other siNAs targeting exon 2 may be used, including siNA targeting positions 420 to 438 of the human htt transcript, such as the shRNA encoded by the sequence aagaactttcagctaccaatctcttgaattggtagctgaaagttctt (SEQ ID NO: 12).

The invention concerns also the use of a siNA molecule or a vector as defined above, for the manufacture of a medicament for preventing or treating Huntington's disease.

The invention provides also a pharmaceutical composition comprising at least a siNA molecule or an expression vector encoding said siNA, as defined above, in an acceptable carrier, such as stabilizer, buffer and the like.

A pharmaceutical composition or formulation refers to a form suitable for administration, e.g., systemic or local administration, into a cell or subject, including a human. Suitable forms, in part, depend upon the use or the route of entry, for example oral, inhalation, or by injection. These compositions or formulations are prepared according to any method known in the art for the manufacture of pharmaceutical compositions.

The invention provides also a siNA molecule or a vector as defined above, as a medicament.

For the purpose of treating or modeling Huntington's disease, as describe above, the siNA molecule or vector is associated with at least one compound that allows the in vivo delivery of the siNA/vector to the target cells (neurons). The compound may be a peptide, antibody, transporter, lipid (neutral or cationic), hydrophobic moiety or a polymer (cationic (PEI) or non-cationic (PEG)). To facilitate delivery into neurons, the siNA/vector may be coupled to Penetratin 1 (Davidson et al., J. Neuroscience, 2004, 24, 10040-10046) or conjugated to cholesterol (Chase et al., Society for Neuroscience Abstract, 2005). To enable the crossing of the blood-brain barrier, the siNA/vector may also be associated with a peptide such as with no limitation the Pep:Trans™ (http://www.syntem.com/english/techpeptrans.html) or with monoclonal antibodies to transferring receptor. To prolong half-life in the circulation, the siNA/vector may be coupled to PEG. To allow specific targeting of the target cells, the siNA/vector may be associated with a ligand of a cell-surface antigen or receptor, for example a peptide or an antibody specific for said antigen/receptor. Examples of such receptors are the adenosine A1/A2, dopamine D1/D2, cannabinoid CB1 and NR2B-type N-methyl D-aspartate (NMDA) receptors.

Preferably, the siNA/vector is associated with a combination of compounds that facilitate the in vivo delivery of the siNA/vector to the target cells (neurons). More preferably, the siNA/vector and the compound(s) are formulated in microspheres, nanoparticles or liposomes.

An effective dose is that dose required to prevent, inhibit the occurrence or treat (alleviate a symptom to some extent, preferably all the symptoms) of a disease or state. The pharmaceutically effective dose of the siNA depends upon the composition used, the route of administration, the physical characteristics of the individual under consideration, concurrent medication, and other factors, that those skilled in the medical arts will recognize. Generally, an amount between 0.1 mg/kg and 100 mg/kg body weight/day of active ingredients is administered.

The siNA of the invention may be administered to human or animal (rodent model) by a single or multiple route(s) chosen from: intracerebral (intrathecal, intraventricular), parenteral (percutaneous, subcutaneous, intravenous, intramuscular, intraperitoneal and intrarachidian), oral, sub-lingual, or inhalation. Preferably; it is administered intracerebrally.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In addition to the preceding features, the invention further comprises other features which will emerge from the description which follows, which refers to examples illustrating the siNA molecules and their uses according to the invention, as well as to the appended drawings in which:

FIG. 1 illustrates the validation of the four shRNA for htt. (A) shRNA constructs were designed to recognized sequences in the 5' end of the human htt transcript. Sihtt1.1 and sihtt3 (which target sequences in exon 2) and sihtt6 (which targets sequences in exons 3 and 4) were used in animal models expressing the first 171 amino acids of the human htt protein, whereas sihtt13 (which targets sequences in exons 8 and 9) was used in animals expressing the first 853 amino acid of the human htt protein. Due to sequence homology between human, rat and mouse htt mRNAs, the shRNAs have different species specificities. Sihtt1.1 recognizes only human htt, sihtt3 and sihtt6 recognize both mouse and human sequences and "universal" sihtt13 recognizes human, rat and mouse htt transcripts. (B) Lentiviral vectors used in this study. Scheme of the lentiviral vectors used to overexpress the first 171 (htt171-82Q) or 853 (htt853-82Q) amino acids of the htt protein. The human htt cDNAs were cloned downstream of the PGK promoter in the SIN-W-PGK transfer vector. Scheme of the lentiviral vectors expressing shRNAs: The different shRNA sequences were inserted in SIN-CWP-nls-LacZ/GFP-LTR-TRE vectors, containing the H1 promoter in the SIN 3'LTR downstream of a tetracycline regulated element (TRE). Transduced cells were identified with the LacZ or GFP reporter genes under the control of the PGK promoter. C. Quantitative real-time PCR analyses showing the silencing of htt mRNA in 293T cells co-expressing htt853-19Q and sihtts 1.1, 3, 6, 13 or the negative control siGFP. Endogenous β-actin mRNA was used as an internal control for the normalization and quantitative analysis of htt mRNA levels 72 hrs after calcium phosphate-mediated transfection. The results are expressed as the mean of relative htt mRNA level±SEM (n=4 htt853-19Q+siGFP, n=6 htt853-19Q+sihtt3, n=7 htt853-19Q+sihtt6 or 13, n=8 htt853-19Q+sihtt1.1). One-way ANOVA, $F(5,32)=14.69$, $P^{*}<0.001$. Newman-Keels Post-hoc comparison between the htt853-19Q±siGFP groups and all sihtt groups are highly significant ($P^{*}<0.001$) whereas there is no significant difference between the htt853-19Q and htt853-19Q/siGFP groups.

Figure 2:
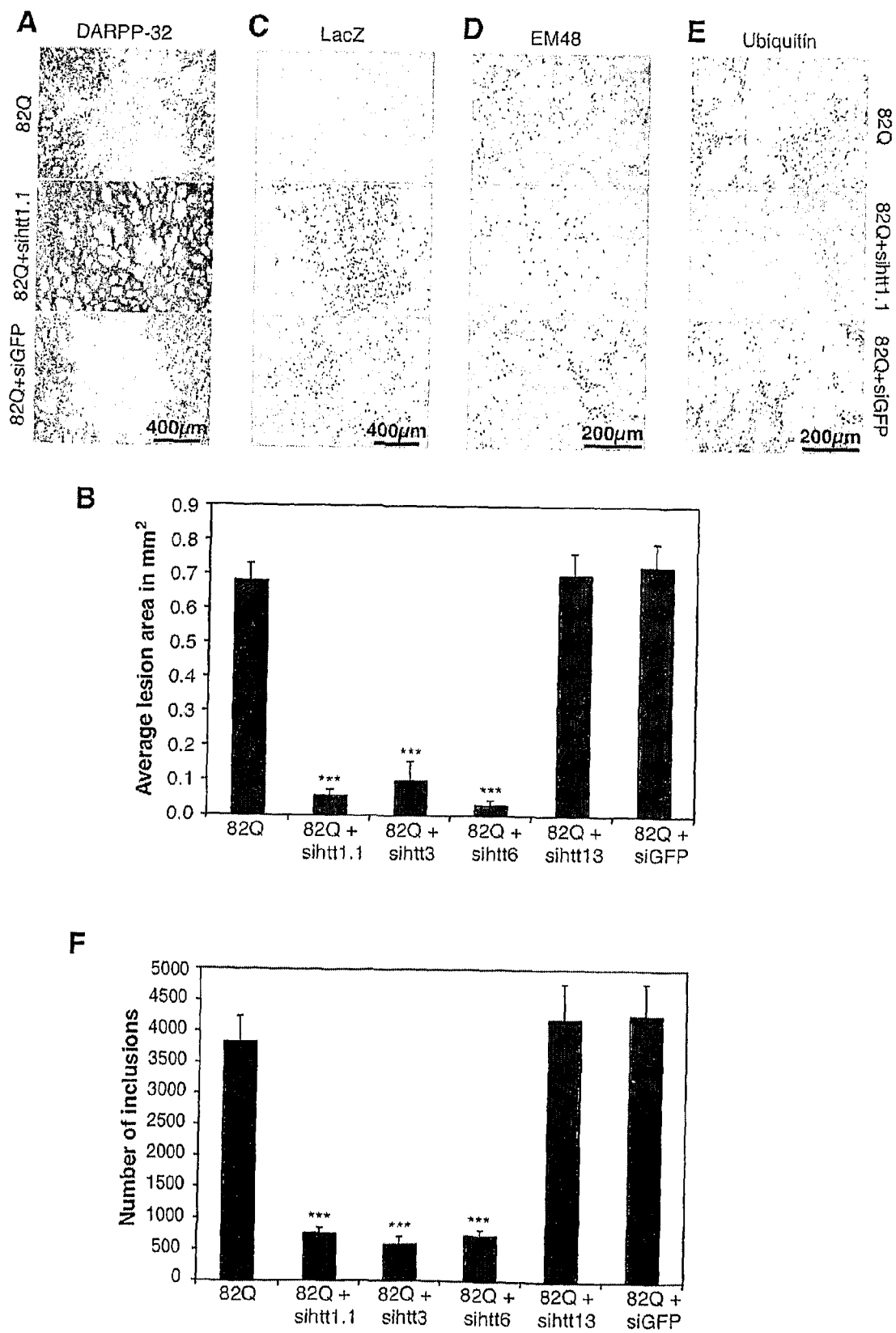

FIG. 2 illustrates the therapeutic efficacy of the shRNA in a rat model of Huntington's disease. Lentiviral-mediated expression of the first 171 amino acid of human htt with 82 glutamine repeats (htt171-82Q) in rat striatum induced a lesion monitored with a DARPP-32 immunostaining. (A) The expression of sihtt1.1 abolished the loss of DARPP-32 expression whereas expression of the control siGFP has no effect. (B) Quantification of the DARPP-32 downregulation induced by htt171-82Q expression (n=9 per group, mean SEM, $P^{*}<0.001$). One-way ANOVA, $F(5,48)=52.97$, $P^{*}<0.001$. Post-hoc comparison of htt171-82Q versus sihtt1.1, 3 and 6 $P^{*}<0.001$. Post-hoc comparison of htt171-82Q versus sihtt13 and siGFP non-significant. (C) LacZ reporter gene expression for the different shRNA constructs. (D-E). EM48 and ubiquitin antibodies were used to assess the formation of htt inclusions. Both staining showed an accumulation of ubiquitinated htt inclusions in animals co-injected with htt171-82Q and siGFP. The expression of sihtt1.1 dramatically reduced the number of immunoreactive cells. (F) Quantification of the number of htt inclusions was based on the ubiquitin staining (n=9 per group for htt171-82Q, htt171-82Q+sihtt6, htt171-82Q+sihtt13 and htt171-82Q+siGFP and n=8 per group for htt171-82Q+sihtt1.1 and htt171-82Q+sihtt3, mean SEM, $P^{*}<0.001$). One-way ANOVA, $F(5,46)=25.16$, $P^{*}<0.001$. Post-hoc comparison of htt171-82Q versus sihtt1.1, 3 and 6 $P^{*}<0.001$. Post-hoc comparison of htt171-82Q versus sihtt13 and siGFP is non-significant.

Figure 3:
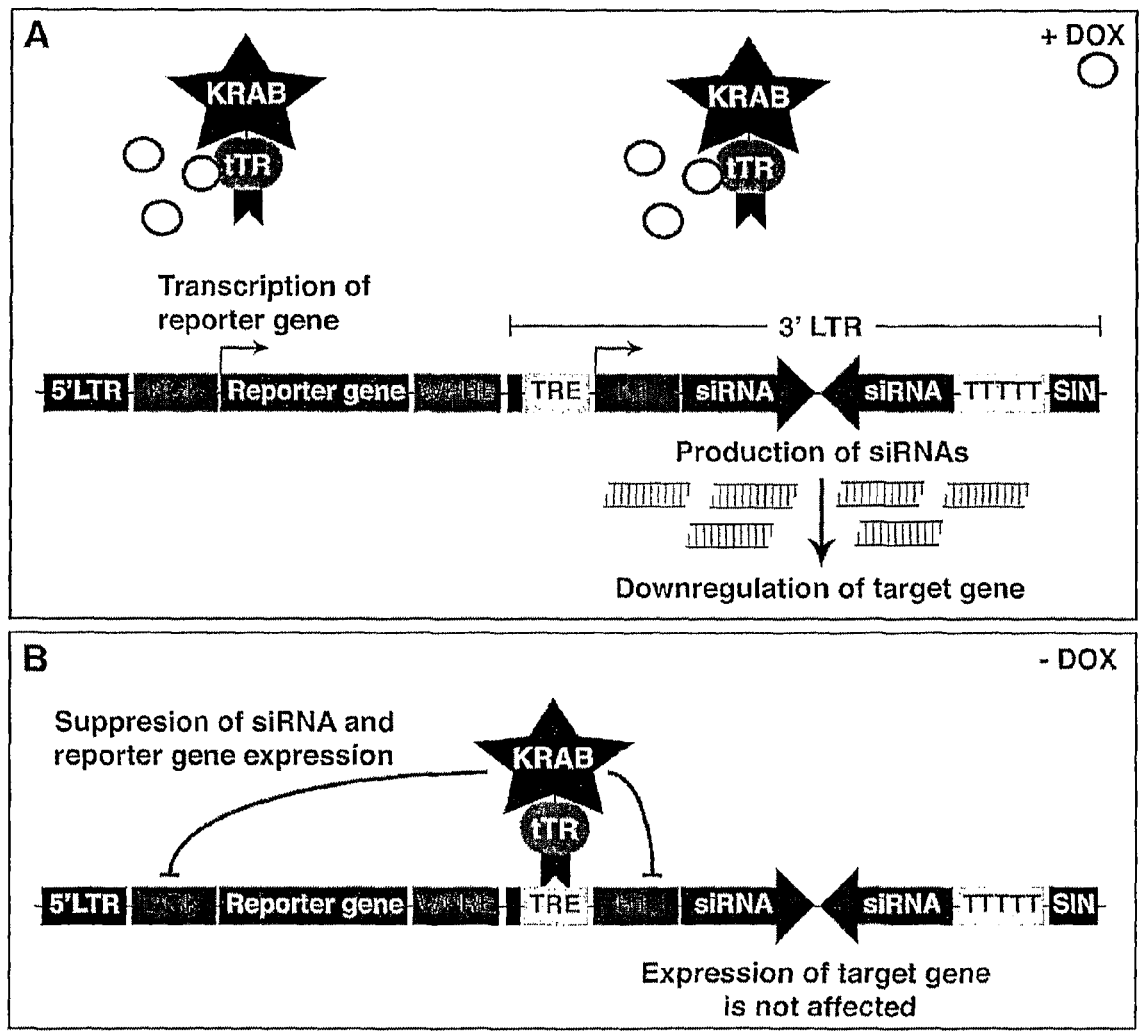

FIG. 3 illustrates regulated expression of siRNA. (A-B) Schematic drawing of the lentivirus vector-based system used for tetracycline-regulated expression. (A) In the presence of doxycycline (+DOX) the tTR-KRAB does not bind the Tetracycline Responsive Element (TRE) located upstream of the H1 promoter driving the expression of the shRNA. The siRNA and the LacZ reporter gene are therefore expressed. (B) In the absence of doxycycline (−DOX), the tTR-KRAB transrepressor binds to the TRE and suppresses H1-mediated siRNA and LacZ reporter gene expression.

Figure 4:
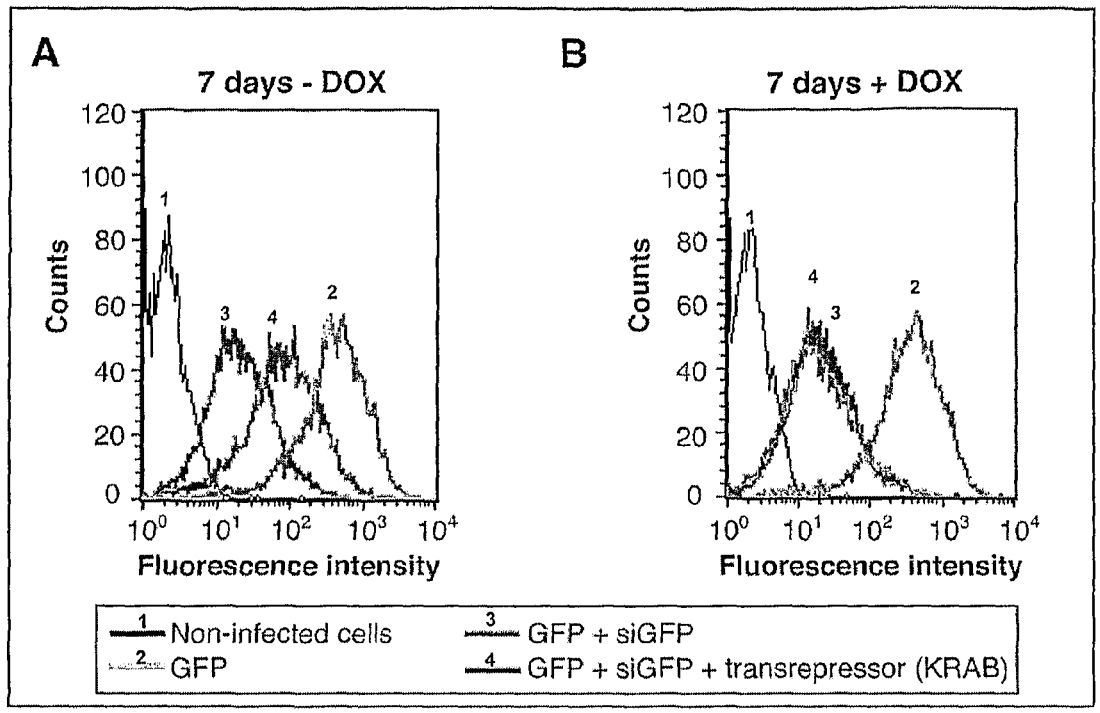
Figure 4:
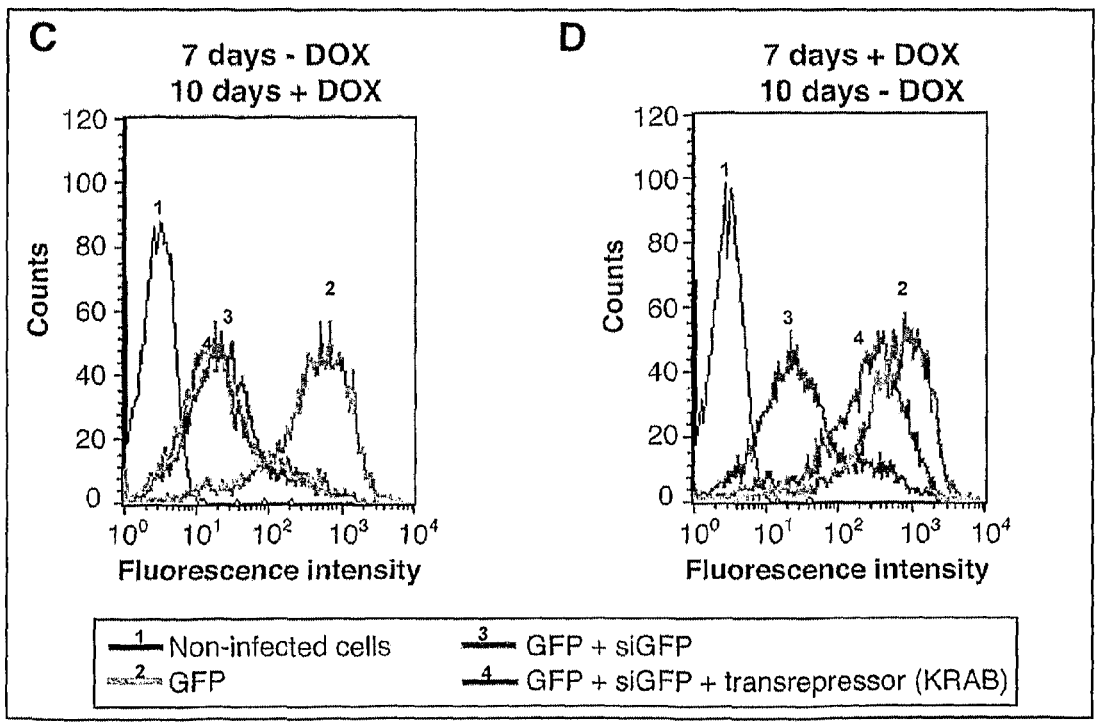

FIG. 4 illustrates the in vitro validation of siGFP regulated expression by FACS analysis. (A-B) FACS analysis of GFP-expressing 293T cells infected with siGFP and KRAB lentiviral vectors. The cells were monitored at 7 days in −DOX (A) and +DOX (B) conditions. In triple-infected (GFP/siGFP/KRAB) cells, the silencing occurred only when the transrepressor activity is inhibited by doxycycline (+DOX). (C-D) To assess the reversibility of the system cells were switched in their DOX condition and maintained for 10 days before a second FACS analysis. The cycling of the expression of the transrepressor KRAB in shown in (C) for −DOX/+DOX and in (D) for +DOX/−DOX. The switch from −DOX to +DOX condition enabled the silencing in triple-infected (GFP/siGFP/KRAB) cells to occur whereas the switch from +DOX to −DOX condition inhibits the expression of siGFP and the mediated GFP silencing.

Figure 5:
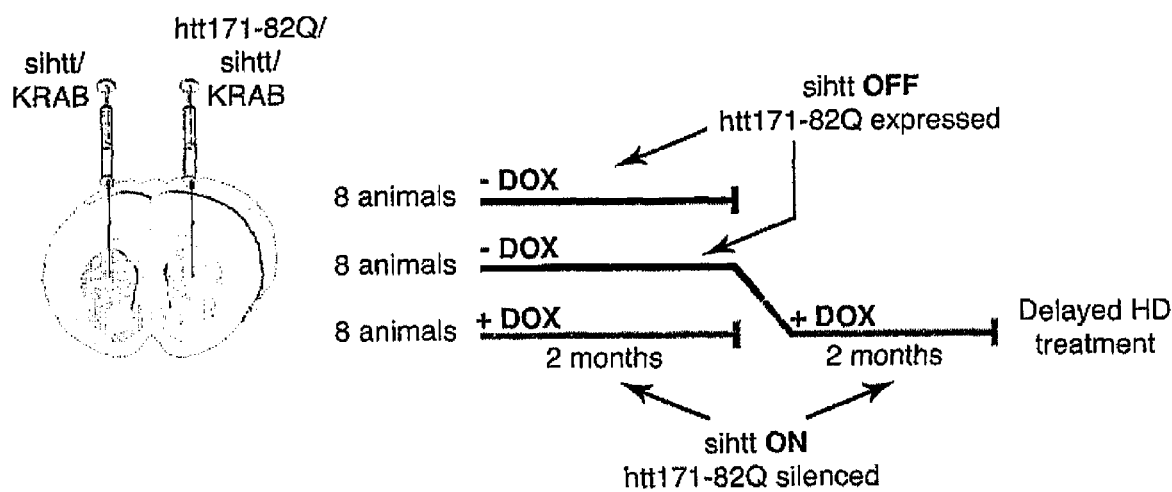

FIG. 5 illustrates the experimental paradigm for the regulated expression of siRNA in vivo. Adults rat were stereotaxically co-injected with lentiviral vectors expressing sihtt1.1/KRAB in the left striatum and triple-injected with vectors expressing htt171-82Q/sihtt1.1/KRAB in the right striatum (n=24). The animals were then divided into three groups of eight animals each. For 2 months, two groups were maintained in the −DOX condition where the sihtt was not expressed, thereby leading to the appearance of Huntington's disease pathology. The third group was treated with doxycycline (+DOX), which led to sihtt and LacZ expression and therefore prevented Huntington's disease pathology. After 2 months, the +DOX animals and half of the rats in −DOX group were sacrificed. DOX treatment was administered in the remaining −DOX animals for another 2 months to mimic a delayed HD treatment.

Figure 6:
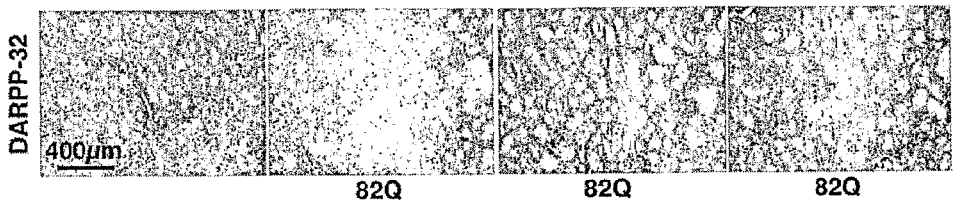
Figure 6:
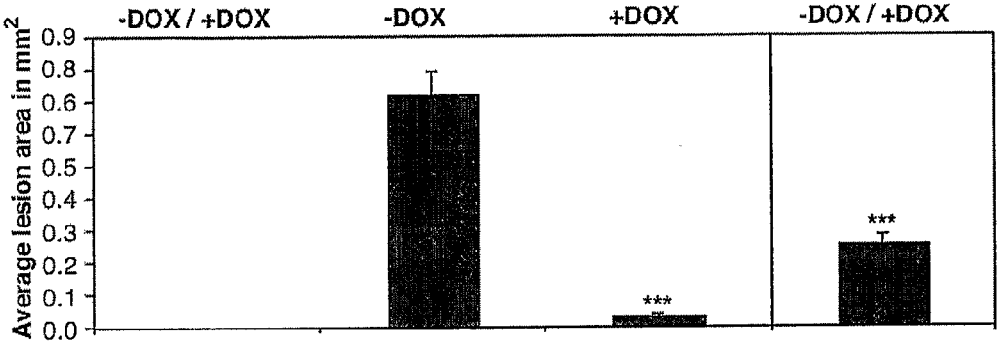
Figure 6:
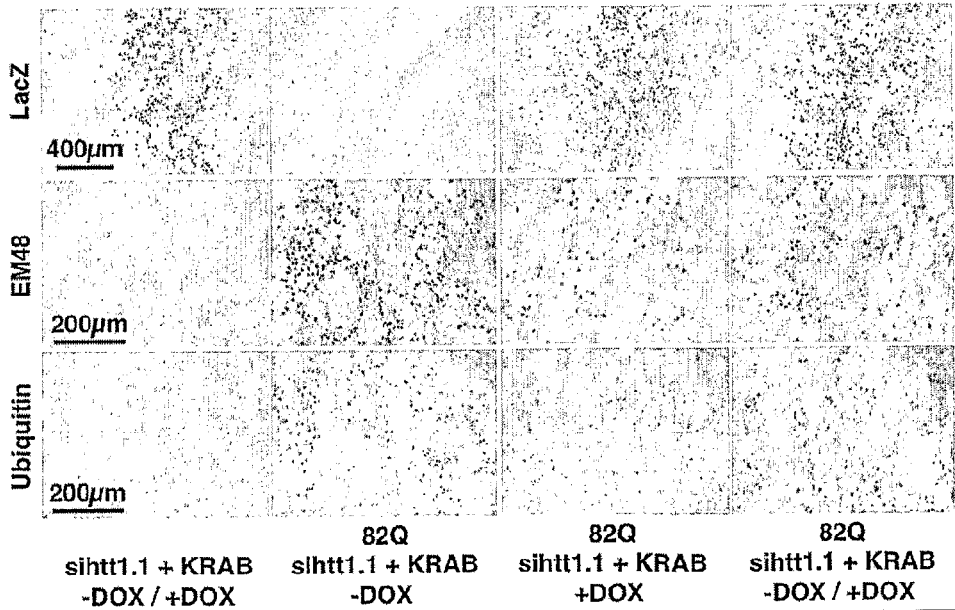
Figure 6:
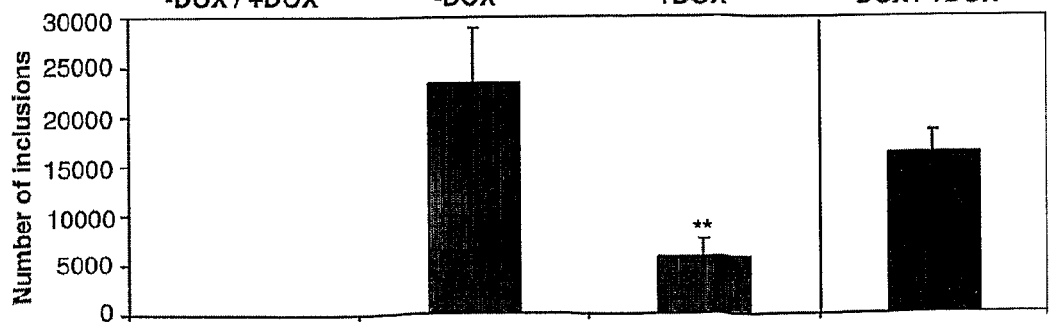

FIG. 6 illustrates the effect of conditional expression of siRNA on HD neuropathology. (A) The DARPP-32 staining was used to monitor the appearance of a striatal pathology. Two months post-injection the typical loss of DARPP-32 expression was observed in −DOX condition whereas the expression of the sihtt1.1 (+DOX condition) almost completely block DARPP-32 downregulation. The expression of sihtt1.1 and the transrepressor KRAB does not alter DARPP-32 expression at 4 months post-injection. In the −DOX/+DOX group, the induction expression of sihtt1.1 after two months significantly rescued DARPP-32 expression. (B) Quantitative analysis of DARPP-32 expression (n=8 per group except for the 82Q/sihtt1.1/KRAB group were n=6 due to mistargeting during stereotaxic injection, mean SEM, $P^{*}<0.001$). One-way ANOVA, $F(3, 26)=34.14$, $P<0.001$. Post-hoc comparison of 82Q/sihtt1.1/KRAB −DOX vs 82Q/sihtt1.1/KRAB +DOX or 82Q/sihtt1.1/KRAB −DOX/+DOX is highly significant; $P^{*}<0.001$. (C) The LacZ reporter gene was used to monitor cells infected with the sihtt1.1 vector. The formation of htt inclusions was assessed with the EM48 and ubiquitin antibodies. A large number of ubiquitinated inclusions were observed at two months for −DOX animals. A residual number of EM48/Ub-positive aggregates were present in +DOX and −DOX/+DOX animals expressing sihtt1.1 as assessed by LacZ staining. (D) Quantitative analysis of the number of lift inclusions was performed from ubiquitin stained sections (n=7 per group for the −DOX, −DOX/+DOX and n=6 per group for the +DOX, mean SEM, $P^{}<0.01$). One-way ANOVA, $F(2,17)=5.39$, $P^{}<0.01$. Post-hoc comparison of +DOX versus −DOX and −DOX/+DOX $P^{**}<0.01$.

Figure 7:
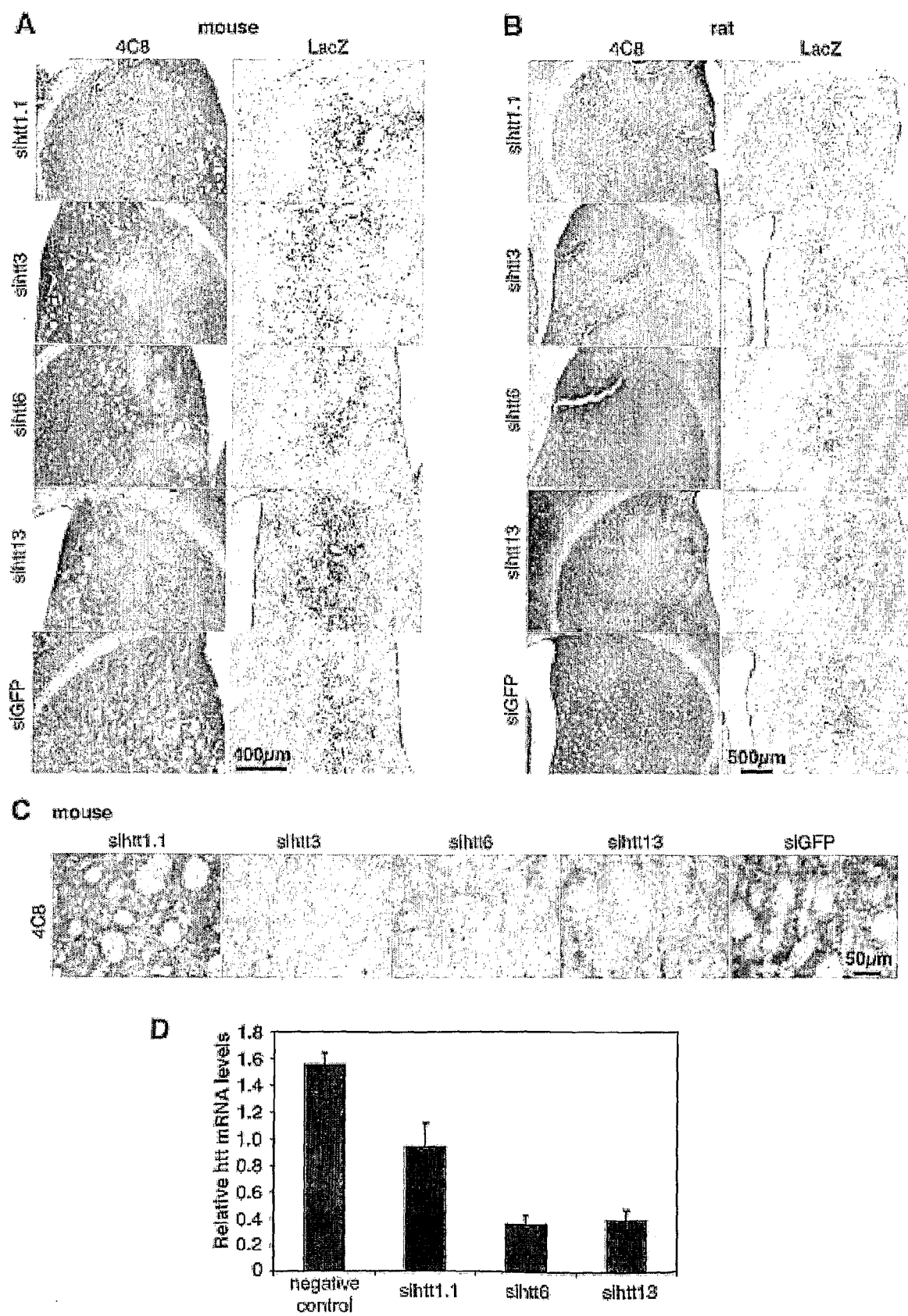

FIG. 7 illustrates the species selectivity of the shRNA in vivo. ShRNA were designed to recognize endogenous htt transcripts in wild-type mouse and rat. After injection of these vectors in mice and rats striatum, endogenous htt staining using the 4C8 antibody was used to evaluate the selectivity of the shRNAs. (A) Expression of sihtt1.1, 3, 6, 13 or control siGFP in mouse striatum. As predicted by their design, sihtt3, 6 and 13 downregulate the expression of the endogenous mouse htt mRNA. No loss of htt expression was observed with sihtt1.1 which is specific for the human transcript or with the control siGFP. A LacZ enzymatic staining was used to identify infected cells. B) Expression of sihtt1.1, 3, 6, 13 or control siGFP in rat striatum. The "universal" sihtt13 vector downregulates the expression of the endogenous rat htt mRNA as monitored by the 4C8 staining. Sihtt1.1 (human specific), sihtt3, 6 (human and mouse specific) and the control siGFP have no affect on endogenous rat htt expression. LacZ enzymatic staining demonstrated that the transduction efficiency was similar in all experimental groups. (C) Higher magnification pictures showing the loss of 4C8 staining in mice injected with sihtt3, 6, 13 and absence of downregulation with the sihtt1.1 and siGFP vectors. (D) RT-PCR on laser microdissected samples from mice striatum injected with sihtt1.1, 6 or 13 and from control striata. The results are expressed as the mean of relative htt mRNA level±SEM (n=7 per group for control, n=6 per group for sihtt1.1 and 13 and n=5 per group for sihtt6). One-way ANOVA, F(3,20)=21.2, P\*\*\*<0.001. Bonferroni/Dunn Post-hoc comparison of control versus sihtt6 and sihtt13 is highly significant, P\*\*\*<0.001. Post-hoc comparisons of control versus sihtt1.1 and sihtt1.1 versus sihtt6 or 13 are significant, P\*\*<0.01.

Figure 8:
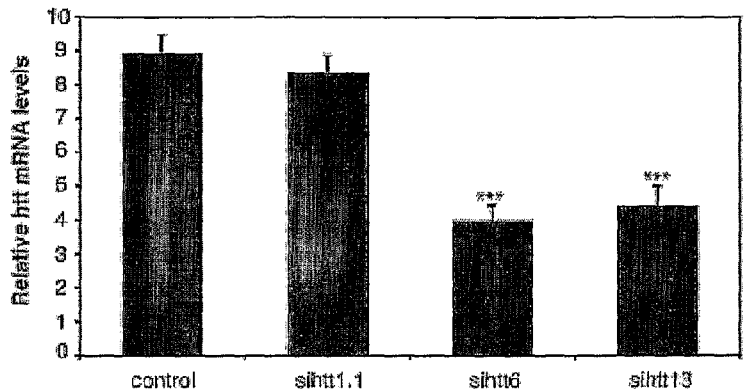
Figure 8:
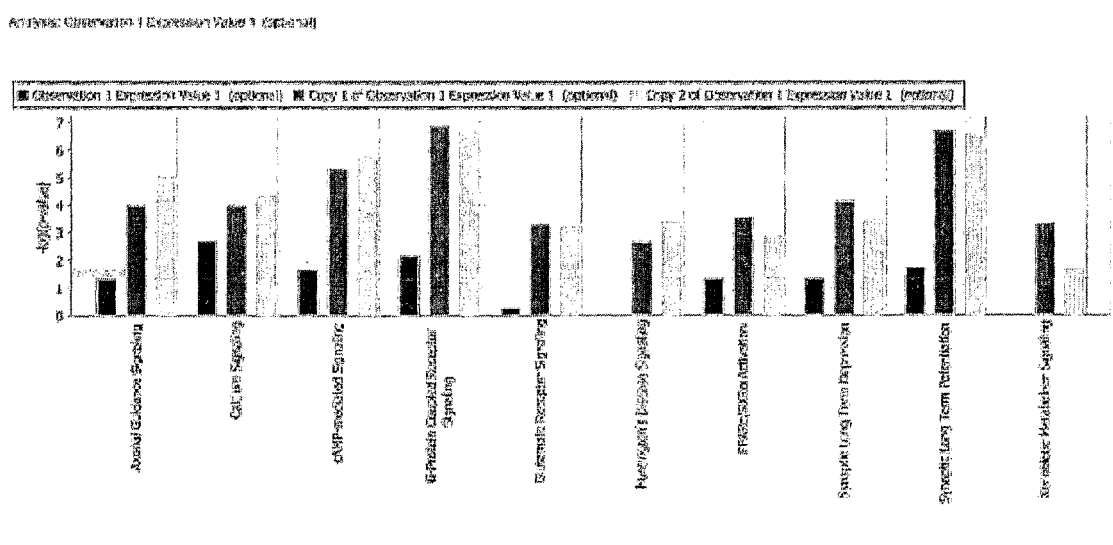

FIG. 8 illustrates the relative change in gene expression following endogenous htt silencing (A) Microarray analysis on laser capture microdissected striatal samples showing the significant reduction in htt expression level in mice injected with the sihtt6 and shtt13 while the human specific sihtt1.1 had no effect. (B) Ingenuity Pathway Analysis on differentially expressed genes showing the biological pathways that are significantly different among sample groups.

Figure 9:
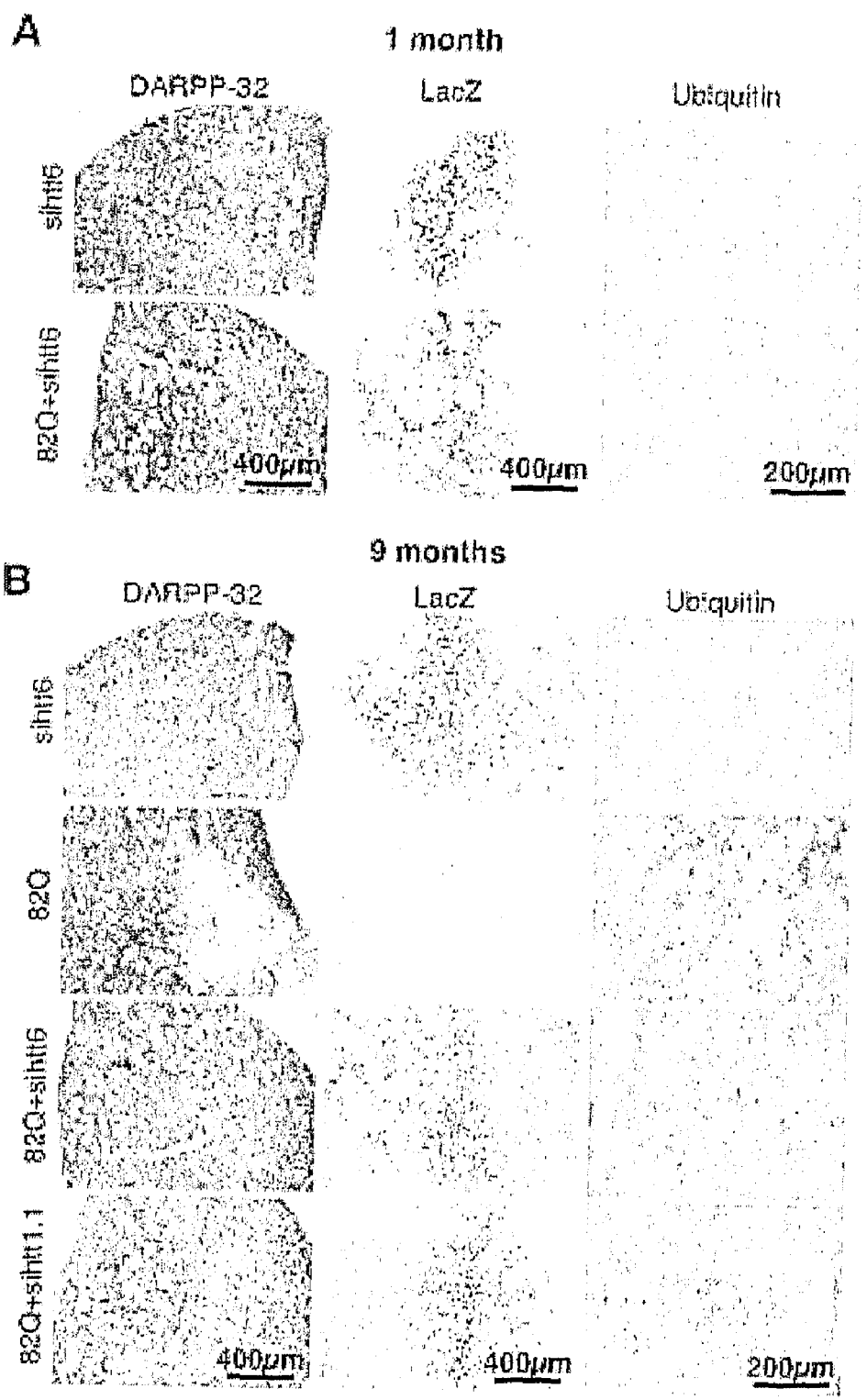

FIG. 9 illustrates long-term effects of global versus mutant-selective htt silencing in mice. Long-term silencing of exogenous mutant htt and/or silencing of the endogenous wild-type protein was assessed in mice injected with lentiviral vectors encoding sihtt1.1 (human, mutant htt specific) and sihtt6 (which targets both normal endogenous mouse htt and exogenous mutant htt). In the sihtt6 group, animals were injected on the left striatum with sihtt6 alone and were co-injected on the right with sihtt6/htt171-82Q. In the sihtt1.1 group, animals were co-injected on the left striatum with sihtt1.1/htt171-82Q vectors and with htt171-82Q on the right. Sihtt6 treated-animals were sacrificed at 1 and 9 months and sihtt1.1-treated animals were sacrificed at 9 months. (A) At one month, cells expressing sihtt6+/−htt171-82Q did not display any change in DARPP-32 staining. The expression of sihtt1.1 and sihtt6 was monitored by LacZ staining, which encompassed a large area of the mouse striatum. (B) At 9 months, expression of sihtt1.1 and 6 prevented htt171-82Q-mediated loss of DARPP-32 expression. Ubiquitin staining, detecting htt inclusions, was present in a large number of htt171-82Q expressing neurons but was almost absent in the striata of animals expressing sihtt1.1 or 6.

Figure 10:
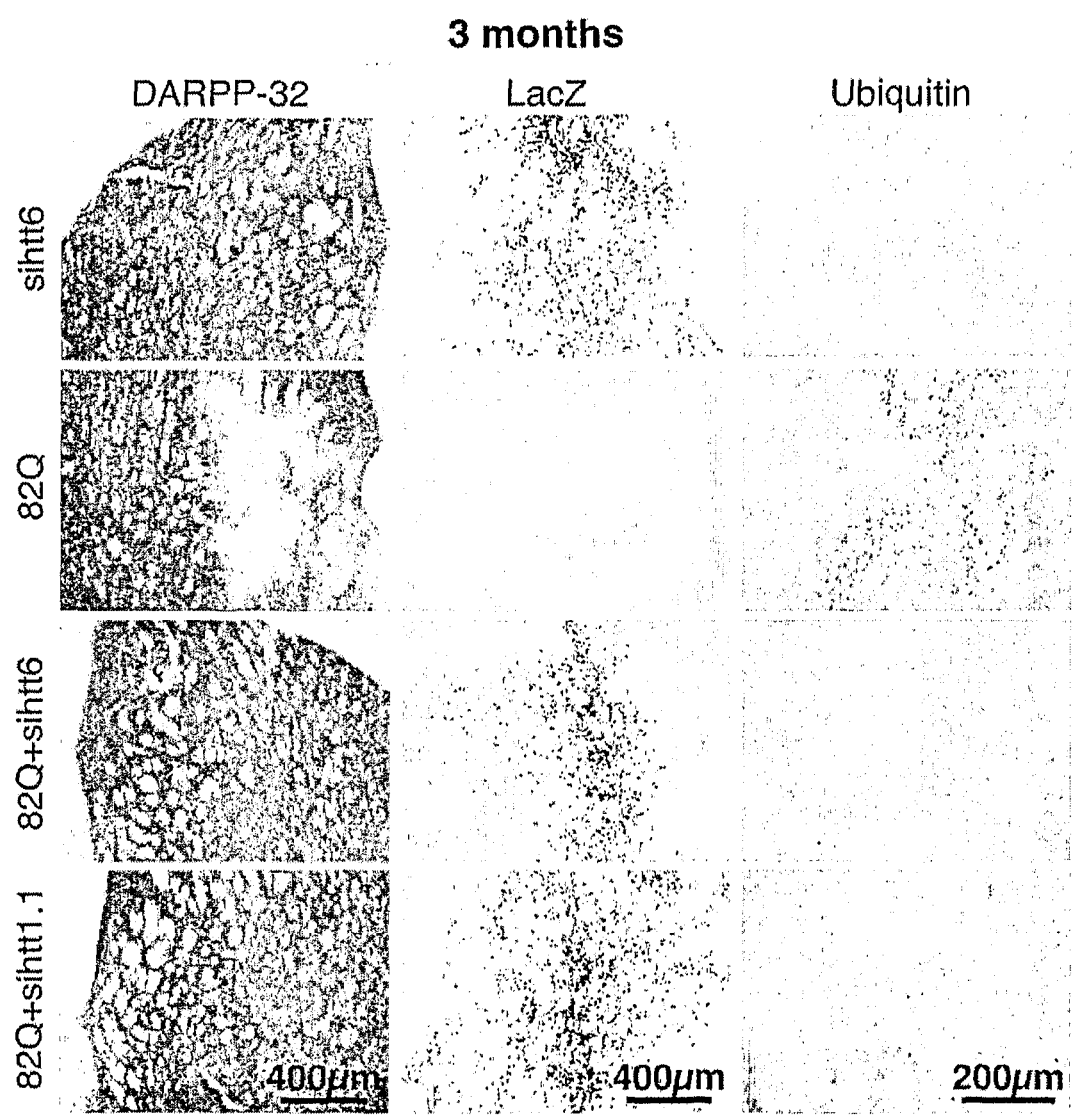

FIG. 10 illustrates long-term global or mutant htt silencing in mice. Long-term silencing of exogenous mutant htt and/or silencing of the endogenous wild-type protein was assessed in mice injected with lentiviral vectors encoding sihtt1.1 (human, mutant htt specific) and sihtt6 (which targets both normal endogenous mouse htt and exogenous mutant). In the sihtt6 group, animals were injected on the left striatum with sihtt6 alone and were co-injected on the right with sihtt6/htt171-82Q. In the sihtt1.1 group, animals were co-injected on the left striatum with sihtt1.1/htt171-82Q vectors and with htt171-82Q on the right. Sihtt6-treated animals were sacrificed at 3 months and sihtt1.1-treated animals were sacrificed at 3 months. At 3 months, expression of sihtt1.1 and 6 prevented htt171-82Q-induced loss of DARPP-32 expression. Ubiquitin staining showed the presence of htt inclusions in a large number of htt171-82Q-expressing neurons but few in the striata of animals coexpressing sihtt1.1 or 6.

Figure 11:
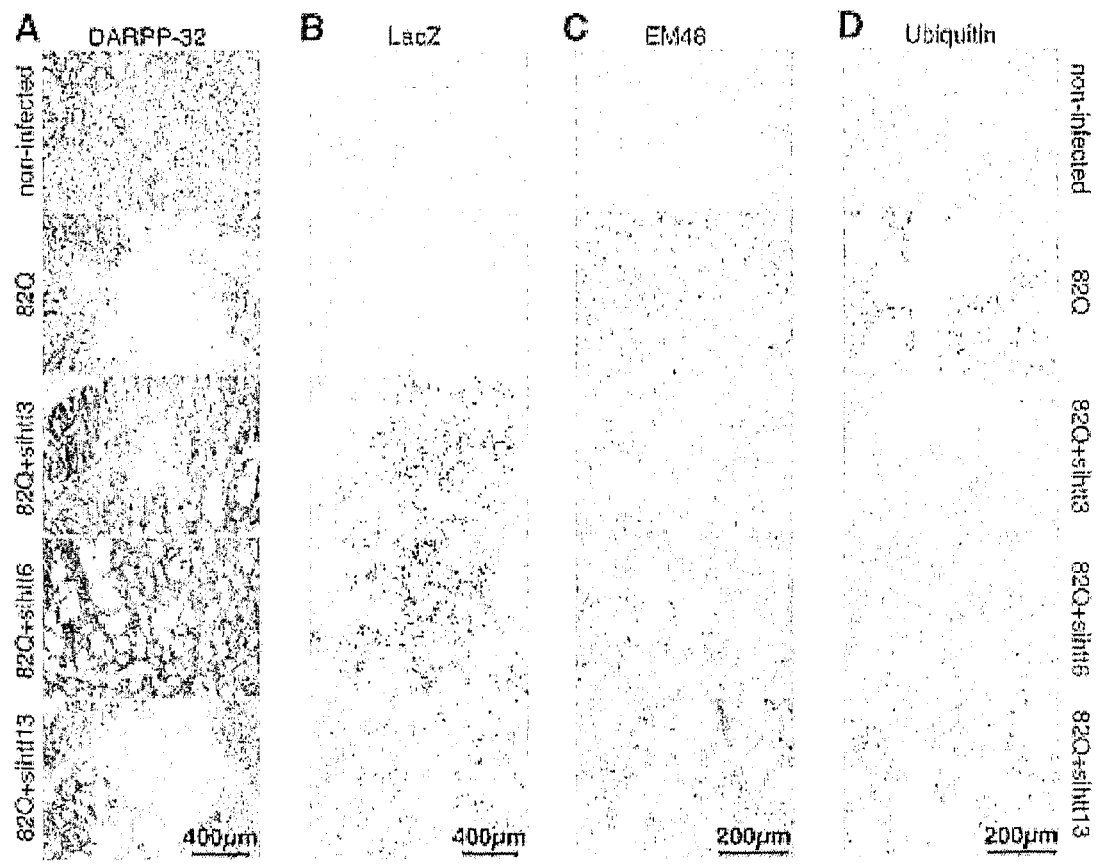

FIG. 11 illustrates the therapeutic efficacy of shRNAs in a rat model of HD. Lentiviral-mediated expression of the first 171 amino acids of human htt with 82 glutamine repeats (htt171-82Q) in rat striatum induced a lesion detected with the DARPP-32 antibody. (A) The expression of sihtt3 and 6 abolished the loss of DARPP-32 expression whereas expression of the control siGFP had no effect. Importantly, the downregulation of endogenous rat htt by sihtt13 in htt171-82Q expressing rats had no effect on the pathology as assessed by DARPP-32 staining. (B) LacZ reporter gene expression for the different shRNA constructs. (C-D). EM48 and ubiquitin antibodies were used to assess the formation of htt inclusions. Both stainings showed an accumulation of ubiquitinated htt inclusions in animals coinjected with htt171-82Q and siGFP, whereas the expression of sihtt3 and 6 dramatically reduced the number of immunoreactive cells.

EXAMPLE 1

Development of Sihtt Lentiviral Vectors

1) Material and Methods
a) Plasmids

Four shRNAs targeting the human htt mRNA were designed with a public algorithm. The first three sequences correspond to exons 1-4 of the human htt gene (sihtt1.1, 3, and 6), and the next one to exons 8-9 (sihtt13). Sihtt3 and 6 are human and mouse specific and sihtt13 is "universal" (human, mouse and rat). Oligonucleotides containing the sense-strand, a loop, the anti-sense strand, the stop codon as well as 17 nucleotides from the H1 promoter were synthesized. As control, a shRNA targeting the EGFP (siGFP) was used.

```
siGFP (SEQ ID NO: 13):
ctagtttccaaaaaagctgaccctgaagttcatctcttgaatgaact
tcagggtcagcttggggatctgtggtctcatacagaac sihtt1.1 (SEQ ID NO: 14):
ctagtttccaaaaaagaactttcagctaccaatctcttgaattggta
gctgaaagttcttggggatctgtggtctcatacagaac sihtt3 (SEQ ID NO: 15):
ctagtttccaaaaaagaccgtgtgaatcattgttctcttgaaacaatg
attcacacggtctggggatctgtggtctcatacagaac sihtt6 (SEQ ID NO: 16):
ctagtttccaaaaaagctttgatggattctaattctcttgaaattaga
atccatcaaagctggggatctgtggtctcatacagaac sitt13 (SEQ ID NO: 17):
ctagtttccaaaaaagcagcttgtccaggtttattctcttgaaataaac
ctggacaagctgcggggatctgtggtctcatacagaac.
```

These oligos and the primer H1-3F: caccgaacgctgacgtcat-caacccg (SEQ ID NO: 18) were used to perform a PCR reaction on the pBC-H1 plasmid (pBC plasmid; STRATAGENE) containing the H1 promoter (Genbank X16612, nucleotides 146-366) as described in Brummelkamp et al., *Science*, 2002, 296, 550-3.

The PCR product was cloned in the pENTR/D-TOPO plasmid (Gateway Technology, INVITROGEN). The H1-shRNA cassette was then transferred with the LR clonase recombination system in the SIN-cPPT-PGK-nls-LacZ-WPRE-LTR-TRE-gateway vector (SIN-CWP-LacZ-TRE-gateway) according to the manufacturer's instructions. This lentiviral vector contains a first expression cassette after the cPPT sequence (Follenzi et al., Nat. Genet., 2000, 25, 217-222) with a nuclear-localized β-galactosidase cDNA (nls-LacZ) under the control of the mouse phosphoglycerate kinase I promoter (PGK). The second expression cassette is located in the SIN 3'LTR (a unique Nod site was inserted in a EcoRV-PvuII deleted 3' U3 region) and contains a modified tetracycline responsive element (TRE) without the CMV minimal promoter (XhoI-StuI from the pTRE-Tight-DsRed2; BD BIOSCIENCES), followed by a gateway cassette (RFA-A conversion cassette; INVITROGEN). To perform the quantitative analysis of endogenous htt in vivo, the sihtt were cloned in a lentiviral vector containing a GFP reporter gene instead of the β-galactosidase (SIN-cPPT-PGK-GFP-WPRE-LTR-gateway vector=SIN-CWP-GFP-gateway). The SIN-W-PGK-TetR(B/E)-KRAB vector was used for doxycycline-regulated shRNA expression. The tetR(B/E)-KRAB fragment was obtained by PCR with the pCMV-tetR(B/E)-KRAB plasmid (Forster et al., *Nucleic Acids Res.*, 1999, 27, 708-710) and the tTRK-1F caccatgtctagattagataaaagt (SEQ ID NO: 19), tTRK-2R ggatccttaaactgatgatttg (SEQ ID NO: 20) oligos. The fragment was cloned in the pENTR/D-TOPO vector (INVITROGEN). A LR clonase reaction was then performed with the pENTR/D-TOPO-tetR(B/E)-KRAB and the SIN-W-PGK-Gateway vector) (RFA-A conversion cassette between the PGK promoter and the WPRE element).

b) Lentiviral Vector Production

Lentiviral vectors encoding the various shRNA, the first 171 or 853 amino acids of human huntingtin with 19 (19Q, wild-type) or 82 (82Q, mutant) CAG repeats (de Almeida et al., *J Neurosci*, 2002, 22, 3473-3483) and the KRAB transrepressor were produced in 293T cells, concentrated by ultracentrifugation and resuspended in phosphate-buffered saline (PBS)/1% bovine serum albumin (BSA) as previously reported (Hottinger et al., *J Neurosci*, 2000, 20, 5587-5593). The viral batches particles content was determined by p24 antigen ELISA (RETROtek, Gentaur, Paris, France). The stocks were stored at −80° C. until use.

c) RT-PCR

HEK 293T cells were cultured in DMEM supplemented with 10% fetal bovine serum (FBS), 100 U/ml penicillin, and 100 µg/ml streptomycin at 37° C. in 5% $CO_2$/air atmosphere. One day prior to transfection, 293T cells were plated at a density of 800'000 cells per well in 6-wells plate (Falcon, BECTON DICKINSON). The cells were co-transfected by calcium phosphate with the SIN-W-PGK-htt853-19Q (1 µg) and sihtt or siGFP vectors (5 µg). Total RNAs were extracted 72 hrs post-transfection with Trizol reagent (INVITROGEN). Real time quantitative RT-PCR was performed in triplicate with 0.4% of random-primed cDNAs generated from 400 ng total RNA. PCR was carried out in a 20 µl reaction volume containing Platinum SYBR Green qPCR super Mix-UDG (INVITROGEN), and 10 µM of both forward (htt-3F tgc cag cac tca aga agg aca c (SEQ ID NO: 21)) and reverse (htt-2R cac gcc aag aat cag cag agt gg (SEQ ID NO: 22)) primers. ABI PRISM 7000 thermal cycler was programmed for an initial denaturation step (95° C., 2 min) followed by 40 amplification cycles (95° C., 15 sec; 60° C., 1 min). The amplification rate of each target was evaluated from the cycle threshold (Ct) numbers obtained for cDNA dilutions and corrected by reference to the expression level of human β-Actin (BACTIN-1F: tgaaggtgacagcagtcggttg (SEQ ID NO: 23); BACTIN-2R: ggcttttaggatggcaagggac (SEQ ID NO:24)) assumed to be constant. Differences between control and experimental samples were calculated using the $2^{-\Delta\Delta ct}$ method (Livak, K. J. and Schmittgen, T. D., *Methods*, 2001, 25, 402-408). LacZ oligos were used as internal standard to assess the efficacy of transfection (LACZ1F: ccttactgccgcctgttttgac (SEQ ID NO: 25); LACZ-2R: tgatgttgaactggaagtcgcc (SEQ ID NO: 26)). The RT-PCR analysis were performed on 6-8 samples from 2-3 independent transfections with the exception of the control with siGFP which was performed on 4 samples from 2 independent experiments. Data are expressed as average of normalized values representing the relative htt mRNA level±SEM. Statistical analysis was performed using one-way analysis of variance (ANOVA) followed by a Newman-Keuls post-hoc test (Statistics 5.1, Statsoft Inc., USA). The significance level was set at $P<0.05$.

2) Results

Four shRNAs targeting the human htt mRNA were designed (FIG. 1A). Sequences in the 5' of the human transcript were specifically selected for three of them (sihtt1.1, 3 and 6) to facilitate the validation in animal models of Huntington's disease. The fourth siRNA, sihtt13, targets a sequence in exons 8-9 of human htt gene. These shRNA were cloned in the SIN-W-PGK-nsl-LacZ-LTR-TRE-H1 lentiviral vector containing a tetracycline-regulated operator upstream of the Hi promoter in the 3'LTR (FIG. 1B). Since the 3'LTR is duplicated upon lentiviral genome insertion in host cell DNA, the presence of two copies of the shRNA expression cassette in infected cells should be leading to higher rate of siRNA synthesis. In addition, a LacZ or a GFP reporter genes were cloned downstream of the internal PGK promoter to identify transduced cells. Co-transfection of 293T cells with a htt853-19Q plasmid and sihtt1.1, 3, 6, 13 or siGFP vectors was used to assess the efficacy of these shRNAs to silence htt. Three days later, cells were harvested and total RNA was isolated. Syber green-based quantitative RT-PCR analysis showed that all sihtt decreased by more than 80% htt mRNA level compared with control samples (htt853-19Q alone or with siGFP) (FIG. 1C). RT-PCR reactions with LacZ oligos confirmed that lentiviral-mediated reduction in htt mRNA reflected the efficiency of the siRNAs and not variation in transfection efficiencies.

EXAMPLE 2

Silencing of Mutant Htt Improves Neuropathology in a Rat Huntington's Disease Model 1) Material and Methods a) In vivo Experiments Animals Adult 180-200g female Wistar rats were used (Iffa Credo/Charles River, Les Oncins, France). The animals were housed in a temperature-controlled room and maintained on a 12 hrs day/night cycle. Food and water were available ad libitum. The experiments were carried out in accordance with the European Community directive (86/609/EEC) for the care and use of laboratory animals.

Lentiviruses Injection

Concentrated viral stocks, prepared as described in example 1, were thawed on ice and resuspended by repeated pipetting. The rats were anesthetized using a ketamine, xylazine solution (75 mg/kg ketamine+10 mg/kg xylazine, i.p). Lentiviral vectors were stereotaxically injected into the striatum of rats using a 34-gauge blunt-tip needle linked to a Hamilton syringe (HAMILTON) by a polyethylene catheter. The stereotaxic coordinates were: 0.5 mm rostral to bregma, 3 mm lateral to midline and 5 mm from the skull surface. The viral particle contents were matched to 480 ng p24 antigen. The viral vectors were injected at 0.2 µl/min by means of an automatic injector (STOELTING Co.) and the needle was left in place for an additional 5 min. The skin was closed using wound chips autoclips (PHYMEP).

b) Histological Processing

Two weeks to six months post-lentiviral injection, the animals received an overdose of sodium pentobarbital and were transcardially perfused with a phosphate solution followed by 4% paraformaldehyde (PAF, FLUKA, SIGMA) and 10% picric acid fixation. The brains were removed and post-fixed in 4% PAF and 10% picric acid for 24 hrs and finally cryoprotected in 25% sucrose, 0.1 M phosphate buffer for 48 hrs. A sledge microtome with a freezing stage of −20° C. (SM2400, LEICA MICROSYSTEMS AG) was used to cut brain coronal sections of 25 µm. Sections throughout the entire striatum were collected and stored free-floating in PBS supplemented with 0.12 µM sodium azide in 96-well plates and stored at 4° C. Striatal sections from injected rats and mice were processed by immunohistochemistry for dopamine and cAMP-regulated phosphoprotein of a molecular mass of 32 kDa (DARPP-32, 1:5000, CHEMICON INTERNATIONAL INC) following the protocol previously described (Bensadoun et al., Eur J Neurosci, 2001, 14, 1753-61). The same protocol was used for ubiquitin (Ub, 1:1000, DAKO-CYTOMATION) with a blocking solution containing 10% fetal calf serum (FCS, GIBCO, INVITROGEN) in addition to NGS. For detection of endogenous htt with the 4C8 antibody (MAB2166, 1:2000, CHEMICON INTERNATIONAL INC.) and mutant htt with EM48 antibody (MAB5374, 1:2000, CHEMICON INTERNATIONAL INC.), slices were pre-incubated for 30 min in 1% sodium cyanoborohydride and rinsed twice in PBS, 0.4% Triton X100 (TX). The first antibody was incubated overnight at room temperature in PBS. Slices were washed 6 times with PBS, 0.4% TX before applying the secondary antibody 2 hrs at room temperature. Biotinylated rabbit anti-goat or horse anti-mouse antibodies (rat absorbed) (1:200; VECTOR LABORATORIES INC) were used for the detection of ubiquitin and EM48, respectively. Bound antibodies were visualized with 3,3' diaminobenzidin (DAB Metal Concentrate; PIERCE) and the ABC amplification system (Vectastain ABC Kit; VECTOR LABORATORIES). The sections were mounted, dehydrated by passing twice through ethanol and toluol solutions, and coverslipped with Eukitt® (O. Kindler, GMBH & CO). For LacZ enzymatic staining, sections were rinsed twice in PBS and incubated for 2 hrs at 37° C. in 4 mM potassium ferrocyanide, 4 mM potassium ferricyanide, 40 mM $MgCl_2$, 0.4 mg/ml 5-bromo-4-chloro-3-indolyl-β-O-galactosidase (X-Gal). The reaction was stopped with PBS.

c) In vivo Data Analysis

For the in vivo experiment, the loss of DARPP-32 expression was analyzed by digitizing twelve sections per animal (150 µm between sections) with a slide scanner and by quantifying the lesion areas in $mm^2$ with an image analysis software (Image J, Version 1.32j, National Institutes of Health). Lesion areas in each section were determined by the area of the region poor in DARP-32 staining relative to the surrounding tissue, Lesion size for each animal is expressed as the mean lesion area in 8-12 sections. Lesion areas for each group are expressed as mean±SEM. Statistical analysis was performed using one-way analysis of variance (ANOVA) followed by a Newman-Keuls post-hoc test (Statistica 5.1, STATSOFT INC.). The significance level was set at $P<0.05$.

d) Quantification of Inclusion Formation

For estimation of the number of ubiquitin-positive htt inclusions, 5-10 serial coronal sections of the striatum (separated by 300 µm) were scanned with a ×10 objective using a Zeiss Axioplan2 imaging microscope equipped with automated motorized stage and acquisition system (Fluovision, IMSTAR). The segmentation of ubiquitin-positive objects throughout the entire section was obtained using light intensity thresholding followed by object's size and shape filtering as previously reported (Palfi et al., Mol. Ther., 2007, 15, 1444-1451). With this procedure, all ubiquitin-positive objects with an apparent cross-sectional area greater than 2 µm2 were reliably detected and cross sectional area was determined. For all images, objects touching one of the X or Y borders of the fields of view were eliminated. We counted from 1 to 1,677 objects/section (depending on the section considered). The estimated total number of objects with ubiquitin-inclusions (Ne) was calculated as Ne=R×Ns, where Ns was the sum of objects counted on all sections, and R (1:12, i.e. 1 every 12 sections) the sampling fraction of striatum. As most ubiquitin-positive objects in striatal neurons were round (mean rotundity index close to one) with an isotropic orientation in the striatum, the number of raw cell counts was corrected using the Abercrombie factor 25. This factor (A) was estimated for each experimental group (values were 0.88-0.92) as A=T/(T+h) where h is the mean object height calculated from all the objects detected and T is the section thickness (25 µm). The corrected number of Ubiquitin positive objects (Nc) was calculated as Nc=A×Ne. Values are expressed as mean±SD. Statistical analysis was performed by one-way analysis of variance (ANOVA) followed by a Bonferroni/Dunn post hoc test (Statview 4.0, Abbacus Concepts, Berkeley, Calif.). Values of $P<0.05$ were considered significant.

2) Results

Rats overexpressing an N-terminal fragment of human htt with 82 CAG repeats (htt171-82Q; de Almeida et al., J. Neurosci., 2002, 22, 3473-3483) were used to evaluate whether siRNAs expression reduced the striatal level of mutant htt and the progression of Huntington's disease pathology (FIGS. 2 and 11). Two months post-injection, the expression of the human htt171-82Q led to the typical loss of the DARPP-32 expression (mean cross-sectional area of DARP-32 poor region=0.68 $mm^2$±0.05) compared with non-injected striata (FIGS. 2A & 2B). Lentiviral-mediated expression of sihtt1.1, 3 and 6 almost completely prevented this loss of DARPP-32 expression (lesion area of 0.06 $mm^2$±0.01, 0.10 $mm^2$±0.05 and 0.03 $mm^2$±0.01, respectively) (FIGS. 2A & 2B; FIG. 11A). This drastic reduction of lesion area (>85%) was specific to the expression of sihtt since DARPP-32 level was unchanged following siGFP expression (0.73 $mm^2$±0.07). The LacZ staining showed that the transduction efficiency was similar in the different experimental groups (FIG. 2C; FIG. 11B). A widespread and intense LacZ expression was observed with the sihtt1.1, 3 and 6 vectors and a large but less intense staining for the siGFP vector. For this latter case, the partial loss of reporter gene expression was due to the ongoing Huntington's disease pathology in these animals (FIG. 2C; FIG. 11C). LacZ staining on striatal sections from siGFP-animals sacrificed at 2 weeks confirmed this interpretation. The impact of shRNA treatment on the number or size of htt inclusions was then examined. In rat overexpressing the human htt171-82Q, EM48 and ubiquitin stainings for mutant htt inclusions were mainly localized in the nuclei of infected neurons, as previously reported (de Almeida, et al., J Neurosci, 2002, 22, 3473-3483), (FIGS. 2D & 2E; FIGS. 11C & 11D). The ubiquitin staining fully corroborated the EM48 data. Comparison of EM48/ubiquitin stainings in htt171-82Q rats and in animals that have received htt171-82Q/siGFP, revealed no differences in the distribution or size of htt inclusions (FIG. 2D). In contrast, a highly significant reduction of number of htt inclusions was observed with sihtt1.1, 3 and 6 (FIGS. 2E & 2F; FIG. 11D). These results show that long-term expression of sihtt1.1, 3 and 6 results in a specific and significant reduction of Huntington's disease pathology in the striatum of adult rats.

EXAMPLE 3

Doxycycline-regulated Expression of Sihtt In vitro

1) Material and Methods

HEK 293T cells were platted at a density of 800'000 cells per well in 6-wells plate (FALCON, BECTON DICKINSON). The cells were infected the following day with the various lentiviral vectors (250 ng p24 antigen/vector) in the presence or the absence of doxycycline (1 µg/ml, SIGMA-ALDRICH). Cells were co-infected (ratio 1:1:1) with SIN-W-PGK-EGFP (enhanced green fluorescent protein, GFP), SIN-CWP-nls-LacZ-TRE-H1-siGFP (siGFP) and the transprepressor SIN-W-PGK-tetR(B/E)-KRAB (KRAB). Cells co-infected with GFP- and siGFP-expressing vectors, cells infected with a vector encoding GFP and non-infected cells were used as controls. Seven days post-infection, 293T cells were harvested and processed for FACS analysis. After trypsinisation, cells were rinsed in PBS and fixed in 1% formaldehyde in PBS. Cell counts were performed in duplicate or triplicate on a FACSCalibur™ analyzer using CellQuest software (BECTON DICKINSON). For each sample, 10'000 events were analyzed. The Mean Fluorescence Intensity (MFI) of GFP-expressing cells was used as internal standard for the normalization of the data. The mean MFI of the different samples was used to measure the efficacy of the siRNA. The data are expressed as mean±SEM from 4 independent experiments. Seven days post-infection, the culture conditions of half of the samples was modified (addition of DOX in samples cultured without DOX and removal of DOX in cultures maintained in DOX) to analyze the reversibility of tetracycline-regulation. A new FACS analysis was performed 10 days later (n=2).

2) Results

As a first step toward the development of conditional expression for siRNA, a tetracycline operator was integrated upstream of the H1 promoter in the lentiviral vectors expressing the siRNA. The co-expression of the TetR-KRAB transrepressor (KRAB) in the presence or absence of doxycycline (DOX) was then used to regulate siRNA expression (Wiznerowicz, M. and Trono, D., *J Virol*, 2003, 77, 8957-61). As described in FIG. 3, the presence of DOX inhibits the binding of the transrepressor to its responsive element (TRE) and enables the expression of the siRNA molecule. In the absence of DOX, the transrepressor is suppressing the expression of the siRNA and LacZ reporter gene. The system was tested on GFP-expressing 293T cells co-infected with vectors encoding siGFP and/or KRAB (FIG. 4). A FACS analysis was performed on cultures maintained 7 days in the absence (FIG. 4A) or presence (FIG. 4B) of DOX. Non-infected (FIGS. 4A and 4B) and GFP-infected cells (FIGS. 4A and 4B) were used as controls. The mean fluorescent intensity (MFI) was significantly reduced in cells expressing the GFP reporter gene and the siGFP (FIGS. 4A and 4B). In triple infected cells (GFP/siGFP/KRAB), the addition of DOX inactivated the transrepressor and led to the silencing of GFP (FIG. 4B; blue curve). In the absence of DOX, the transrepressor was active and GFP expression was maintained although the MFI was lower than in control cells infected with the GFP alone (FIG. 4A). This might reflect the intrinsic leakiness of the system and the split of the system in 3 vectors. To demonstrate the reversibility of the system, DOX treatment was switched after 7 days and a new FACS analysis was performed 10 days later (FIGS. 4C and 4D). A complete reversal of FACS profile was observed 10 days after the switch in DOX treatment on cells. This experiment demonstrated the proof and principle for doxycycline-regulated expression of shRNAs.

EXAMPLE 4

Delivery of SiRNA at a Symptomatic Stage of Huntington's Disease Pathology in Rat Led to Neuroprotective Effects 1) Material and Methods
Animals The rats used were as described in example 2. For tetracycline-regulated experiments, the animals received a solution of 200 mg/l doxycycline (DOX, SIGMA CHEMICAL CO.) and 15 g/l sucrose in their drinking water.
Lentiviruses Injection The experimental procedures were as described in example 2; for double and triple infections, the viral particle contents were matched to 500 and 338 ng p24 antigen, respectively.
Histological Processing The experimental procedures were as described in example 2.

2) Results

The sihtt1.1 was chosen to validate the conditional regulation of siRNA in vivo. The sihtt1.1 was selected to assess whether the efficacy of sihtt treatment is altered if initiated after the appearance of Huntington's disease pathology. To this aim, rats were injected with a mixture of lentiviral vectors expressing htt-171-82Q, sihtt1.1 and KRAB (1:1:1 ratio) in the right striatum. A mixture of sihtt1.1 and KRAB vectors were injected in the left striatum (FIG. 5) as control of protein toxicity and expression level. The first two groups (n=8 per group) were maintained without doxycycline (−DOX; "OFF") and a third group received doxycycline (+DOX; "ON"). After 2 months, animals in the "ON" group (+DOX) and half of the animals from the "OFF" group (−DOX) were sacrificed. DOX administration was then switched in the remaining animals for the following 2 months (−DOX/+DOX). The expression of sihtt1.1 and the functionality of the tetracycline transrepressor (KRAB) were indirectly monitored with the LacZ reporter gene (FIG. 6C). In the "ON" animals, a LacZ staining was observed in a large area around the injection site. In "OFF" condition, the KRAB transrepressor induced a remodeling of the chromatin and a repression of LacZ expression, as previously reported (FIG. 2; Wiznerowicz, M. and Trono, D., *J Virol*, 2003, 77, 8957-8961). At 2 months, the "OFF" only animals (no siRNA expression) displayed the typical HD pathology (FIGS. 2A & 2B) with a loss of DARPP-32 expression in the left striatum (0.72 mm$^2$±0.07) (FIGS. 6A and 6B). However, some residual DARPP-32 expression was observed in the lesion size (FIG. 6A). This reflects the basal expression of sihtt1.1 in the "off" condition and the fact that all neurons did not co-express htt171-82Q, sihtt1.1 and KRAB. In the "ON" only group, the efficacy of the siRNA treatment was in agreement with the results reported in FIG. 2, with a drastic reduction of lesion size (to 0.03 mm$^2$±0.01) (FIG. 6B) and a lower number of ubiquitin-positive inclusions (78.1±6.6%; FIG. 6D). Importantly, initiating the sihtt1.1 treatment two months after the onset of the pathology significantly reduced the loss of DARP-32 expression (0.25 mm$^2$±0.03) and is associated with a partial clearance of htt inclusions (34.1±8.4%; FIGS. 6B &

6C & 6D). These data further establish the reversibility of polyQ-induced striatal pathology and demonstrate that a treatment initiated after neuropathological disease onset is still effective in diminishing polyQ-mediated toxicity.

EXAMPLE 5

Design and Validation of ShRNA Targeting Endogenous Wild-type Htt

1) Material and Methods
Animals

The rats used were as described in example 2. Adult 26g female C57/BL6 mice were used (IFFA CREDO/CHARLES RIVER). The animals were housed as described in example 1.
Lentiviruses Injection The experimental procedures for rats were as described in example 2. The experimental procedures for mice were similar to that described in example 2 for rats, with the exception that: (i) the stereotaxic coordinates were: 0.6 mm rostral to bregma 1.8 mm lateral to midline and 3.5 mm from the skull surface for the intrastriatal injection in mice; (ii) concentrated viruses were matched to 160 ng p24 antigen, and (iii) the skin was closed using 4-0 Prolene® suture (Ethicon, Johnson and Johnson, Brussels, Belgium).
Histological Processing The experimental procedures were as described in example 2.
Laser Microdissection and RT-PCR in Mice Two microliters of SIN-CWP-GFP-sihtt1.1 (n=6), SIN-CWP-GFP-sihtt6 (n=6), and SIN-CWP-GFP-sihtt13 (n=6) were injected in the striatum of adult mice. The animals were sacrificed 16 weeks post-injection by the administration of an overdose of pentobarbital (150 mg/kg, intravenously; Sanofi, France). The brains were immediately removed, freezed in cold 2-methylbutane, sectioned in the coronal plane on a freezing microtome (14 μm sections) and stored at −80° C. The dehydration of the sections was performed using 30 s incubations in graded ethanols (75%, 95%, 100%, 100%) and 5 min in xylene. Slides were placed in vacuum desiccator with fresh desiccant and store at room temp until to perform Laser Capture Microdissection (LCM) with a PixCell® IIe Arcturus® instrument. The green fluorescence of the GFP reporter gene was used to identify the area of the striatum infected with the vectors. LCM Laser Capture Microdissection System using laser spot size 30 μm, 46 mW and with 3.3 ms duration. After visual control of the completeness of laser microdissection (onto the thermoplastic film), the captured tissue was extracted using Rneasy Micro Kit (Qiagen, Hilden, Germany) following the manufacturer's instructions. The nucleotide acid concentration is determined by Quant-iT™ RNA Assay Kit (Molecular Probes™ Invitrogen, Carlsbad, Calif., USA) and the integrity was determined using Agilent RNA 6000 Pico Labchip (Agilent Technologies, Wadbrown, Germany). Thirty ng of total RNA were used as starting material for the RT-PCR. In order to limit dissection time for higher efficiency and RNA quality, we dissect only enough tissue to yield approximately 80-180 ng of total RNA per animal (8-20 sections), which is sufficient for both RT-PCR and microarray analysis. The reverse transcription was performed as follows: 1 μl oligo-dT was added to the samples and incubated at 70° C., 5 min. Six microliters of MIX (ABgene Reverse-iT MAX RTase blend) was then added (4 μl buffer, 1 μl dNTP 10 mM, 1 μl enzyme Reverse-iT max RTase blend) and the samples were incubated at 42° C. for 60 min. The PCR reaction was performed with the FastStart DNA Master SYBR Green I kit (Roche, Diagnostics GmbH, Mannheim, Germany) and a set of oligos targeting an area around the sequences of sihtt13 (htt C: ggggtgacacggaaagaaat (SEQ ID NO: 27) and D: tcagtgcttgcaggagttca (SEQ ID NO: 28)). The reaction was performed as follows: 1.5 μl light cycler DNA Master SYBER Green, 3-5 mM $MgCl_2$, 0.4 μM primers in 20 μl, 45 cycles of 8 min at 95° C., 5 min at 68° C., and 8 min at 72° C. The cyclophilin gene was used as internal standard (oligos: CYCLO-1F: atggcaaatgctggaccaaa (SEQ ID NO: 29); CYCLO-2R: gccttctttcaccttcccaaa (SEQ ID NO: 30)). Amplification graphs were checked for the cross-point ($C_t$) value of the PCR product. The $C_t$ value represented the cycle by which the fluorescence of a sample increased to a level higher than the background fluorescence in the amplification cycle. Melting curve analysis was performed after PCR amplification to verify that the correct product was amplified by examining its specific melting temperature (Tm). Relative quantification was made by the standard curve method. A series of dilutions of calibrator sample (external standard) was included in each experiment in order to generate an external standard curve. That curve is used for quantification of both target and housekeeping gene (endogenous control) in each sample, for input normalization. Relative quantification was carried out using RealQuant Software (version 1.01, Roche). The calculation of data is based on the CP values obtained by the LightCycler® Software. Results are calculated as the target/reference ratio of the sample divided by the target/reference ratio of the calibrator. This corrects for sample inhomogeneity and variability of detection.
2) Results The next set of experiments take advantage of the species-selectivity of the siRNA constructs to investigate whether a partial downregulation of endogenous htt can be tolerated in adult animals and to provide information on the possible necessity of an allele-specific htt silencing. Based on sequence identity, the sihtt1.1 should target only the human htt transcript, the sihtt3 and sihtt6 target the human and mouse htt (1-2 mismatches with the rat sequence) and the sihtt13, which targets a conserved sequence, should cause RNAi-mediated diminution of the human, rat and mouse htt transcripts. To confirm this predicted selectivity of the sihtts, these vectors were injected in the striatum of normal adult mice and rats. Immunohistochemical analysis of striatal sections 3 weeks post-surgery established the species-selectivity of the siRNA on endogenous htt transcript (FIG. 7). The LacZ reporter gene allowed the identification of transduced neurons and the 4C8 antibody was used detect the endogenous htt protein. In all cases, LacZ-positive cells were present around the injection sites and no significant differences in immunoreactivity were observed between the shRNA vectors (FIGS. 7A and 7B). As expected, siGFP and sihtt1.1 vectors have no effect on endogenous levels of mouse and rat htt (FIGS. 7A and 7B). The sihtt13 led to a downregulation of endogenous mouse and rat htt (FIGS. 7A and 7B). A reduced htt immunoreactivity was also observed in the striatum of mice injected with sihtt 3, and 6 while these siRNAs have no effect in rats due to the presence of 1-2 mismatches in the sequences. These data were confirmed by LacZ/htt double staining and confocal analysis. To further quantify the level of in vivo silencing, new vectors expressing the GFP reporter gene and the sihtt1.1, sihtt6 or sihtt13 were developed. These vectors were injected in adult mice and laser microdissection and RT-PCR analysis were performed on striatal sections 16 weeks post-injection. Silencing of endogenous htt to 24±3.5% and 26±4.9% of normal levels were obtained with the sihtt6 and sihtt13, respectively while the sihtt1.1, which is human specific, had a limited impact on the wild-type mouse htt (63±11.8%) (FIG. 7D). These data also demonstrates that these vectors efficiently silenced not only exogenously administered mutant htt (FIGS. 2 and 11) but also endogenous htt transcript.

EXAMPLE 6

Comparison of Selective Versus Non-selective Knockdown of Mutant and Wildtype Htt Alleles in Rats and Mice 1) Material and Methods
Animals The rats used were as described in example 2. Adult 26g female C57/BL6 mice were used (IFFA CREDO/CHARLES RIVER). The animals were housed as described in example 1.
Lentiviruses Injection The experimental procedures for rats were as described in example 2. The experimental procedures for mice were similar to that described in example 2 for rats, with the exception that, in mice: (i) the stereotaxic coordinates for the intrastriatal injection were: 0.6 mm rostral to bregma 1.8 mm lateral to midline and 3.5 mm from the skull surface; (ii) concentrated viruses were matched to 160 and 130 ng p24 antigen for single and double infections, respectively, and (iii) the skin was closed using 4-0 Prolene® suture (Ethicon, Johnson and Johnson, Brussels, Belgium).
Histological Processing The experimental procedures were as described in example 2.
In vivo Data Analysis The experimental procedures were as described in example 2.
Codelink Microarray Processing and microarray analysis were done on the technological plateform profileXpert (www.profilexpert.fr).
RNA Amplification Total RNA (15 ng) was amplified by two rounds of in vitro transcription (dIVT) and biotin-labeled with a Message Amp™ II aRNA kit (AMBION) following the manufacturer's protocol. Before amplification, spikes of synthetic mRNA at different concentrations were added to all samples; these positive controls were used to ascertain the quality of the process. aRNA yield was measured with an UV spectrophotometer and the quality on nanochips with the Agilent 2100 Bioanalyzer (AGILENT).
Array Hybridization and Processing Ten micrograms of biotin-labeled aRNA was fragmented using 5 µl of fragmentation buffer in a final volume of 20 µl, then was mixed with 240 µl of Amersham hybridization solution (GE HEALTHCARE EUROPE GMBH) and injected onto CodeLink Uniset Human Whole Genome bioarrays containing 55000 human oligonucleotide gene probes or CodeLink Uniset Rat Whole Genome bioarrays containing 36000 rat oligonucleotide gene probes (both from GE HEALTHCARE EUROPE GMBH). Arrays were hybridized overnight at 37° C. at 300 rpm in an incubator. The slides were washed in stringent TNT buffer at 46° C. for 1 hour, then a streptavidin-cy5 (GE HEALTHCARE) detection step was performed. Each slide was incubated for 30 min in 3.4 ml of streptavidin-cy5 solution, then was washed 4 times in 240 ml of TNT buffer, rinsed twice in 240 ml of water containing 0.2% Triton X-100, and dried by centrifugation at 600 rpm. The slides were scanned using a Genepix 4000B scanner (AXON) and Genepix software, with the laser set at 635 mm, the laser power at 100%, and the photomultiplier tube voltage at 60%. The scanned image files were analyzed using CodeLink expression software, version 4.0 (GE HEALTH-CARE), which produces both a raw and normalized hybridization signal for each spot on the array.
Microarray Data Analysis The relative intensity of the raw hybridization signal on arrays varies in different experiments. CodeLink software was therefore used to normalize the raw hybridization signal on each array to the median of the array (median intensity is 1 after normalization) for better cross-array comparison. The threshold of detection was calculated using the normalized signal intensity of the 100 negative control samples in the array; spots with signal intensities below this threshold are referred to as "absent". Quality of processing was evaluated by generating scatter plots of positive signal distribution. Signal intensities were then converted to log base 2 values. Statistical comparison and filtering were performed using Genespring software 7.0 (AGILENT). Ingenuity Pathway Analysis (MOUNTAIN VIEW) was used for function analysis.
Quantification of LacZ Expression Sections were digitized as 8-bit gray-scale images with a flatbed scanner (ImageScanner, GE HEALTHCARE EUROPE) and the relative optical density was determined using an image analysis software (MCID, INTERFOCUS IMAGING). Data are expressed as mean OD calculated from 4 sections centered on the injection site. Regions of interest (ROI) were drawn according to the LacZ staining. Data are expressed as mean OD calculated from the ROI of 4 sections per animal, centered on the injection site.
2) Results To evaluate the consequences of endogenous htt silencing in adult brains, a microarray analyses of RNA expression was performed on laser capture microdissected brain sections from adult mice injected with lentiviral vectors expressing sihtt1.1, sihtt6 or sihtt13 (SIN-CWP-GFP-sihtt). The GFP reporter gene was used to identify infected cells. Microarray quantification of mouse htt mRNA levels corresponded to the selectivities of the three siRNAs (FIG. 8A). Significant reductions in mouse htt were observed with the sihtt6 and shtt13 while the human specific sihtt1.1 had no effect (FIG. 8A). Using ingenuity pathway analysis on differentially expressed genes revealed that the injection of the control lentiviral vector sihtt1.1 was associated with only modest changes in striatal expression profile. These subtle changes are consistent with a local scarring/wound healing response to the surgical procedure, but did not comprise a RNAi-mediated activation of the interferon response (Bridge et al., Nat. Genet., 2003, 34, 263-264), as demonstrated by an absence of effects on the interferon-regulated genes AOS, PKR and LTR. In contrast, the expression of sihtt6 and sihtt13 induced significant changes in the expression of specific non-inflammatory genes. The expression profiles of the sihtt6 and sihtt13 were highly correlated indicating that the silencing effect is very specific and thus "off-target" effects are very limited. Moreover, the specific genes whose expression was altered by htt silencing were observed to participate in molecular pathways linked to known htt functions including G-protein coupled receptor signaling, synaptic long term potentiation/depression, axonal guidance, cAMPmediated signaling, and calcium and glutamate signaling (Cattaneo et al., Nat. Rev. Neurosci., 2005, 6, 919-930; Harjes et al., Trends Biochem. Sci., 2003, 28, 425-433).

To investigate the functional consequences of such a donwregulation of endogenous rat htt in the context of HD, a first experiment was performed, in which adult rats were co-infected with vectors encoding the human htt171-82Q and the sihtt13 or human htt171-82Q alone. The sihtt13 targets sequences in exons 8 and 9 which are not present in the htt171-82Q vector (FIG. 1A). With this experimental paradigm, a selective silencing of wild-type rat htt is achieved in animals expressing the mutant human htt171-82Q. Two months post-injection, the animals were sacrificed and the effect of endogenous sihtt silencing was analyzed. No differences were seen between htt171-82Q/sihtt13 and htt171-82Q groups in term of GABAergic neuron survival based on DARPP-32 expression (htt171-82Q: 0.68 mm$^2$±0.05; htt171-82Q and sihtt13: 0.70 mm$^2$±0.06) or htt inclusion load (FIGS. 2A, 2B, 2D and 2E). These data suggest that a partial inactivation of the endogenous htt has no major impact on the course of Huntington's disease pathology.

To further evaluate the long-term impact of global inactivation of wild-type and mutant htt versus a selective knockdown of the disease allele, the selectivity of sihtt1.1 for the human form of htt and the non-selectivity of the sihtt6 which recognizes both human and mouse endogenous htt, were used. These siRNA were co-injected with human htt171-82Q in the striata of mice and the animals were sacrificed at 1, 3 and 9 months post-injection. Both sihtt dramatically reduced Huntington's disease pathology (assessed by DARPP-32 and ubiquitin stainings) to the same extent (FIGS. 9A & 9B and 10). Also, numbers of Lac2 positive cells were similar in both groups, supporting that the survival of GABAergic is not affected by the silencing of endogenous mouse htt (FIGS. 9A & 9B and 10). These results also indicate that sihtt6 expression level was not limiting (i.e. that the silencing of mutant htt was not inhibited by coincident silencing of wild-type htt). Altogether, these data suggest that coincident non allele-specific silencing is effective against HD pathology and that a partial inactivation of wild-type htt is well tolerated.

The invention claimed is:

1. An isolated double-stranded short interfering nucleic acid molecule comprising complementary sense and antisense regions, wherein:
   the antisense region has 15 to no more than 19 contiguous nucleotides that are complementary to a human huntingtin transcript, said nucleotides being encoded by a sequence selected from the group consisting of SEQ ID NO: 1, SEQ ID NO: 2, and SEQ ID NO: 3,
   the sense and antisense regions have at least 15 contiguous nucleotides that are complementary to each other and form a duplex, and
   said double-stranded short interfering nucleic acid molecule inhibits the expression of endogenous wild-type and exogenous human mutant huntingtin genes in cells of a non-human mammal which are expressing both said huntingtin genes.

2. The double-stranded short interfering nucleic acid molecule according to claim 1, wherein the sense region comprises at least 15 contiguous nucleotides that are encoded by a sequence selected from the group consisting of SEQ ID NO: 4, SEQ ID NO: 5, and SEQ ID NO: 6.

3. The double-stranded short interfering nucleic acid molecule according to claim 1, which is assembled from two separate oligonucleotides, each of 15 to about 30 nucleotides, to form a duplex structure of at least 15 base pairs.

4. The double-stranded short interfering nucleic acid molecule according to claim 1, which is assembled from a single oligonucleotide of 31 to about 50 nucleotides, to form a hairpin having a duplex structure of at least 15 base pairs and a loop structure of 4 to 10 nucleotides.

5. The double-stranded short interfering nucleic acid molecule according to claim 4, wherein the loop is encoded by SEQ ID NO: 7.

6. The double-stranded short interfering nucleic acid molecule according to claim 5 which is encoded by a sequence selected from the group consisting of SEQ ID NO: 8, SEQ ID NO: 9, and SEQ ID NO: 10.

7. The double-stranded short interfering nucleic acid molecule according to claim 1, wherein one or both 3' end(s) comprise(s) 1 to about 3 overhanging nucleotides.

8. The double-stranded short interfering nucleic acid molecule according to claim 1, wherein both ends are blunt.

9. The double-stranded short interfering nucleic acid molecule according to claim 1, which is an RNA molecule.

10. The double-stranded short interfering nucleic acid molecule according to claim 1, which comprises one or more modified pyrimidine and/or purine nucleotides.

11. The double-stranded short interfering nucleic acid molecule according to claim 1, which comprises at least one modified internucleotidic linkage.

12. The double-stranded short interfering nucleic acid molecule according to claim 1, wherein said non-human mammal is a mouse or a rat.

13. A transcription unit comprising: a transcription initiation region, a transcription termination region, and a nucleic acid sequence encoding at least one short interfering nucleic acid molecule molecule according to claim 1, wherein said nucleic acid sequence is operably linked to said initiation region in a manner that allows expression and/or delivery of the short interfering nucleic acid molecule in a host cell.

14. The transcription unit according to claim 13, wherein the transcription initiation region comprises a doxycycline regulated promoter.

15. An expression vector comprising a transcription unit according to claim 13.

16. The expression vector according to claim 15, which is a replication-defective and multiply attenuated lentiviral vector.

17. A cell which is modified by a vector according to claim 16.

18. A pharmaceutical composition comprising at least one short interfering nucleic acid molecule according to claim 1 in an acceptable carrier.

19. A method for preventing or treating Huntington's disease comprising administering the short interfering nucleic acid molecule according to claim 1 to a subject.

20. A method to study Huntington's disease in a rodent model comprising contacting the short interfering nucleic acid molecule according to claim 1 to a cell of the rodent model.

* * * * *

SEQUENCE LISTING

```
<160> NUMBER OF SEQ ID NOS: 30

<210> SEQ ID NO 1
<211> LENGTH: 19
<212> TYPE: DNA
<213> ORGANISM: Artificial
<220> FEATURE:
<223> OTHER INFORMATION: siNA molecule

<400> SEQUENCE: 1
tctggcacac ttagtaaca                                                    19

<210> SEQ ID NO 2
<211> LENGTH: 19
<212> TYPE: DNA
<213> ORGANISM: Artificial
<220> FEATURE:
<223> OTHER INFORMATION: siNA molecule

<400> SEQUENCE: 2
tcgaaactac ctaagatta                                                    19

<210> SEQ ID NO 3
<211> LENGTH: 19
<212> TYPE: DNA
<213> ORGANISM: Artificial
<220> FEATURE:
<223> OTHER INFORMATION: siNA molecule

<400> SEQUENCE: 3
cgtcgaacag gtccaaata                                                    19

<210> SEQ ID NO 4
<211> LENGTH: 19
<212> TYPE: DNA
<213> ORGANISM: Artificial
<220> FEATURE:
<223> OTHER INFORMATION: siNA molecule

<400> SEQUENCE: 4
agaccgtgtg aatcattgt                                                    19

<210> SEQ ID NO 5
<211> LENGTH: 19
<212> TYPE: DNA
<213> ORGANISM: Artificial
<220> FEATURE:
<223> OTHER INFORMATION: siNA molecule
```

```
<400> SEQUENCE: 5
agctttgatg gattctaat                                                    19

<210> SEQ ID NO 6
<211> LENGTH: 19
<212> TYPE: DNA
<213> ORGANISM: Artificial
<220> FEATURE:
<223> OTHER INFORMATION: siNA molecule

<400> SEQUENCE: 6
gcagcttgtc caggtttat                                                    19

<210> SEQ ID NO 7
<211> LENGTH: 9
<212> TYPE: DNA
<213> ORGANISM: Artificial
<220> FEATURE:
<223> OTHER INFORMATION: loop structure comprised in siNA molecule

<400> SEQUENCE: 7 ttcaagaga                                                                9

<210> SEQ ID NO 8
<211> LENGTH: 47
<212> TYPE: DNA
<213> ORGANISM: Artificial
<220> FEATURE:
<223> OTHER INFORMATION: shNA molecule

<400> SEQUENCE: 8
agaccgtgtg aatcattgtt tcaagagaac aatgattcac acggtct                     47

<210> SEQ ID NO 9
<211> LENGTH: 47
<212> TYPE: DNA
<213> ORGANISM: Artificial
<220> FEATURE:
<223> OTHER INFORMATION: shNA molecule

<400> SEQUENCE: 9
agctttgatg gattctaatt tcaagagaat tagaatccat caaagct                     47

<210> SEQ ID NO 10
<211> LENGTH: 47
<212> TYPE: DNA
<213> ORGANISM: Artificial
<220> FEATURE:
<223> OTHER INFORMATION: shNA molecule

<400> SEQUENCE: 10
gcagcttgtc caggtttatt tcaagagaat aaacctggac aagctgc                     47

<210> SEQ ID NO 11
<211> LENGTH: 13481
<212> TYPE: DNA
<213> ORGANISM: Homo sapiens

<400> SEQUENCE: 11
gctgccggga cgggtccaag atggacggcc gctcaggttc tgcttttacc tgcggcccag       60
agccccattc attgccccgg tgctgagcgg cgccgcgagt cggcccgagg cctccgggga      120
ctgccgtgcc gggcgggaga ccgccatggc gaccctggaa aagctgatga aggccttcga      180
gtccctcaag tccttccagc agcagcagca gcagcagcag cagcagcagc agcagcagca      240
```

```
gcagcagcag cagcagcagc aacagccgcc accgccgccg ccgccgccgc cgcctcctca    300
gcttcctcag ccgccgccgc aggcacagcc gctgctgcct cagccgcagc cgccccgcc     360
gccgccccg ccgccacccg gcccggctgt ggctgaggag ccgctgcacc gaccaaagaa     420
agaactttca gctaccaaga aagaccgtgt gaatcattgt ctgacaatat gtgaaaacat    480
agtggcacag tctgtcagaa attctccaga atttcagaaa cttctgggca tcgctatgga    540
acttttctg ctgtgcagtg atgacgcaga gtcagatgtc aggatggtgg ctgacgaatg     600
cctcaacaaa gttatcaaag ctttgatgga ttctaatctt ccaaggttac agctcgagct    660
ctataaggaa attaaaaaga atggtgcccc tcggagtttg cgtgctgccc tgtggaggtt    720
tgctgagctg gctcacctgg ttcggcctca gaaatgcagg ccttacctgg tgaaccttct    780
gccgtgcctg actcgaacaa gcaagagacc cgaagaatca gtccaggaga ccttggctgc    840
agctgttccc aaaattatgg cttcttttgg caattttgca aatgacaatg aaattaaggt    900
tttgttaaag gccttcatag cgaacctgaa gtcaagctcc cccaccattc ggcggacagc    960
ggctggatca gcagtgagca ctgccagca ctcaagaagg acacaatatt tctatagttg    1020
gctactaaat gtgctcttag gcttactcgt tcctgtcgag gatgaacact ccactctgct    1080
gattcttggc gtgctgctca ccctgaggta tttggtgccc ttgctgcagc agcaggtcaa    1140
ggacacaagc ctgaaaggca gcttcggagt gacaaggaaa gaaatggaag tctctccttc    1200
tgcagagcag cttgtccagg tttatgaact gacgttacat catacacagc accaagacca    1260
caatgttgtg accggagccc tggagctgtt gcagcagctc ttcagaacgc tccacccga    1320
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
atgcagccct gtcctttcaa gaaaacaaaa aggcaaagtg ctcttaggag aagaagaagc    1500
cttggaggat gactctgaat cgagatcgga tgtcagcagc tctgccttaa cagcctcagt    1560
gaaggatgag atcagtggag agctggctgc ttcttcaggg gtttccactc cagggtcagc    1620
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt accccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat ttgtgttgag    2100
agatgaagct actgaaccgg gtgatcaaga aaacaagcct tgccgcatca aggtgacat     2160
tggacagtcc actgatgatg actctgcacc tcttgtccat tgtgtccgcc ttttatctgc    2220
ttcgttttg ctaacagggg gaaaaaatgt gctggttccg gacagggatg tgagggtcag    2280
cgtgaaggcc ctggccctca gctgtgtggg agcagctgtg gccctccacc cggaatcttt    2340
cttcagcaaa ctctataaag ttcctcttga caccacggaa taccctgagg aacagtatgt    2400
ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
```

```
gaggaactgt gtcatgagtc tctgcagcag cagctacagt gagttaggac tgcagctgat    2700
catcgatgtg ctgactctga ggaacagttc ctattggctg gtgaggacag agcttctgga    2760
aacccttgca gagattgact tcaggctggt gagcttttttg gaggcaaaag cagaaaactt   2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgtttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taaccttttca agagttattg cagcagtttc    3180
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aaccccccttt ctctaagtcc catccgacga aaggggaagg agaaagaacc    3720
aggagaacaa gcatctgtac cgttgagtcc caagaaaggc agtgaggcca gtgcagcttc    3780
tagacaatct gataccctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt cttttctcaga tactagagct ggccacactg caggacattg ggaagtgtgt    4020
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggtttttaga    4500 tttgctggcg cagctggttc agttacgggt taattactgt cttctggatt cagatcaggt    4560
gtttattggc tttgtattga aacagtttga atacattgaa gtgggccagt tcagggaatc    4620
agaggcaatc attccaaaca tcttttttctt cttggtatta ctatcttatg aacgctatca    4680
ttcaaaacag atcattggaa ttcctaaaat cattcagctc tgtgatggca tcatggccag    4740
tggaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
```

```
ccttggagtg ttaaatacat tatttgagat tttggcccct tcctccctcc gtccggtaga    5100
catgctttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta aagaacaca gtgaagggaa     5340
acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg aatgtgcaa     5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccaggcaa ttcagtctcg ttgtgaaaac ctttcaactc caaccatgct    6060
gaagaaaact cttcagtgct tggagggat ccatctcagc cagtcgggag ctgtgctcac     6120
gctgtatgtg gacaggcttc tgtgcacccc tttccgtgtg ctggctcgca tggtcgacat    6180
ccttgcttgt cgccgggtag aaatgcttct ggctgcaaat ttacagagca gcatggccca    6240
gttgccaatg gaagaactca acagaatcca ggaataccct cagagcagcg ggctcgctca    6300
gagacaccaa aggctctatt ccctgctgga caggtttcgt ctctccacca tgcaagactc    6360
acttagtccc tctcctccag tctcttccca cccgctggac ggggatgggc acgtgtcact    6420
ggaaacagtg agtccggaca aagactggta cgttcatctt gtcaaatccc agtgttggac    6480
caggtcagat tctgcactgc tggaaggtgc agagctggtg aatcggattc ctgctgaaga    6540
tatgaatgcc ttcatgatga actcggagtt caacctaagc ctgctagctc catgcttaag    6600
cctagggatg agtgaaattt ctggtggcca gaagagtgcc cttttttgaag cagcccgtga    6660
ggtgactctg gcccgtgtga gcggcaccgt gcagcagctc cctgctgtcc atcatgtctt    6720
ccagcccgag ctgcctgcag agccggcggc ctactggagc aagttgaatg atctgtttgg    6780
ggatgctgca ctgtatcagt ccctgcccac tctggcccgg gccctggcac agtacctggt    6840
ggtggtctcc aaactgccca gtcatttgca ccttcctcct gagaaagaga aggacattgt    6900
gaaattcgtg gtggcaaccc ttgaggccct gtcctggca ttgatccatg agcagatccc     6960
gctgagtctg gatctccagg cagggctgga ctgctgctgc ctggccctgc agctgcctgg    7020
cctctggagc gtggtctcct ccacagagtt tgtgacccac gcctgctccc tcatctactg    7080
tgtgcacttc atcctggagg ccgttgcagt gcagcctgga gagcagcttc ttagtccaga    7140
aagaaggaca ataccccaa aagccatcag cgaggaggag gaggaagtag atccaaacac     7200
acagaatcct aagtatatca ctgcagcctg tgagatggtg gcagaaatgg tggagtctct    7260
gcagtcggtg ttggccttgg gtcataaaag gaatagcggc gtgccggcgt ttctcacgcc    7320
attgctaagg aacatcatca tcagcctggc ccgcctgccc cttgtcaaca gctacacacg    7380
tgtgccccca ctggtgtgga agcttggatg gtcacccaaa ccgggagggg attttggcac    7440
```

| | |
|---|---|
| agcattccct gagatcccg tggagttcct ccaggaaaag gaagtctttta aggagttcat | 7500 |
| ctaccgcatc aacacactag gctggaccag tcgtactcag tttgaagaaa cttgggccac | 7560 |
| cctccttggt gtcctggtga cgcagcccct cgtgatggag caggaggaga gcccaccaga | 7620 |
| agaagacaca gagaggaccc agatcaacgt cctggccgtg caggccatca cctcactggt | 7680 |
| gctcagtgca atgactgtgc ctgtggccgg caacccagct gtaagctgct tggagcagca | 7740 |
| gccccggaac aagcctctga aagctctcga caccaggttt gggaggaagc tgagcattat | 7800 |
| cagagggatt gtggagcaag agattcaagc aatggtttca aagagagaga atattgccac | 7860 |
| ccatcattta tatcaggcat gggatcctgt cccttctctg tctccggcta ctacaggtgc | 7920 |
| cctcatcagc cacgagaagc tgctgctaca gatcaacccc gagcgggagc tggggagcat | 7980 |
| gagctacaaa ctcggccagg tgtccataca ctccgtgtgg ctggggaaca gcatcacacc | 8040 |
| cctgagggag gaggaatggg acgaggaaga ggaggaggag gccgacgccc ctgcaccttc | 8100 |
| gtcaccaccc acgtctccag tcaactccag gaaacaccgg gctggagttg acatccactc | 8160 |
| ctgttcgcag ttttttgcttg agttgtacag ccgctggatc ctgccgtcca gctcagccag | 8220 |
| gaggaccccg gccatcctga tcagtgaggt ggtcagatcc cttctagtgg tctcagactt | 8280 |
| gttcaccgag cgcaaccagt ttgagctgat gtatgtgacg ctgacagaac tgcgaagggt | 8340 |
| gcacccttca gaagacgaga tcctcgctca gtacctggtg cctgccacct gcaaggcagc | 8400 |
| tgccgtcctt gggatggaca aggccgtggc ggagcctgtc agccgcctgc tggagagcac | 8460 |
| gctcaggagc agccacctgc ccagcagggt tggagccctg cacggcgtcc tctatgtgct | 8520 |
| ggagtgcgac ctgctggacg acactgccaa gcagctcatc ccggtcatca gcgactatct | 8580 |
| cctctccaac ctgaaaggga tcgcccactg cgtgaacatt cacagccagc agcacgtact | 8640 |
| ggtcatgtgt gccactgcgt tttacctcat tgagaactat cctctggacg tagggccgga | 8700 |
| attttcagca tcaataatac agatgtgtgg ggtgatgctg tctggaagtg aggagtccac | 8760 |
| cccctccatc atttaccact gtgccctcag aggcctggag cgcctcctgc tctctgagca | 8820 |
| gctctcccgc ctggatgcag aatcgctggt caagctgagt gtggacagag tgaacgtgca | 8880 |
| cagcccgcac cgggccatgg cggctctggg cctgatgctc acctgcatgt acacaggaaa | 8940 |
| ggagaaagtc agtccgggta gaacttcaga ccctaatcct gcagccccg acagcgagtc | 9000 |
| agtgattgtt gctatggagc gggtatctgt tcttttttgat aggatcagga aaggctttcc | 9060 |
| ttgtgaagcc agagtggtgg ccaggatcct gccccagttt ctagacgact tcttcccacc | 9120 |
| ccaggacatc atgaacaaag tcatcggaga gtttctgtcc aaccagcagc catacccca | 9180 |
| gttcatggcc accgtggtgt ataaggtgtt tcagactctg cacagcaccg gcagtcgtc | 9240 |
| catggtccgg gactgggtca tgctgtccct ctccaacttc acgcagaggg ccccggtcgc | 9300 |
| catgccacg tggagcctct cctgcttctt tgtcagcgcg tccaccagcc cgtgggtcgc | 9360 |
| ggcgatcctc ccacatgtca tcagcaggat gggcaagctg gagcaggtgg acgtgaacct | 9420 |
| tttctgcctg gtcgccacag acttctacag acaccagata gaggaggagc tcgaccgcag | 9480 |
| ggccttccag tctgtgcttg aggtggttgc agccccagga agcccatatc accggctgct | 9540 |
| gacttgttta cgaaatgtcc acaaggtcac cacctgctga gcgccatggt gggagagact | 9600 |
| gtgaggcggc agctggggcc ggagcctttg gaagtctgcg cccttgtgcc ctgcctccac | 9660 |
| cgagccagct tggtccctat gggcttccgc acatgccgcg ggcggccagg caacgtgcgt | 9720 |
| gtctctgcca tgtggcagaa gtgctctttg tggcagtggc caggcaggga gtgtctgcag | 9780 |
| tcctggtggg gctgagcctg aggccttcca gaaagcagga gcagctgtgc tgcaccccat | 9840 |

```
gtgggtgacc aggtcctttc tcctgatagt cacctgctgg ttgttgccag gttgcagctg   9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctcttcctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
agtgggcagg tggccacagc aggactgagg acaggccccc attatcctag gggtgcgctc  10440
acctgcagcc cctcctcctc gggcacagac gactgtcgtt ctccaccccac cagtcaggga  10500 cagcagcctc cctgtcactc agctgagaag gccagccctc cctggctgtg agcagcctcc  10560
actgtgtcca gagacatggg cctcccactc ctgttccttg ctagccctgg ggtggcgtct  10620
gcctaggagc tggctggcag gtgttgggac ctgctgctcc atggatgcat gccctaagag  10680
tgtcactgag ctgtgttttg tctgagcctc tctcggtcaa cagcaaagct tggtgtcttg  10740
gcactgttag tgacagagcc cagcatccct tctgcccccg ttccagctga catcttgcac  10800
ggtgacccct tttagtcagg agagtgcaga tctgtgctca tcggagactg ccccacggcc  10860
ctgtcagagc cgccactcct atccccaggc caggtccctg gaccagcctc ctgtttgcag  10920
gcccagagga gccaagtcat taaaatggaa gtggattctg gatggccggg ctgctgctga  10980
tgtaggagct ggatttggga gctctgcttg ccgactggct gtgagacgag caggggctc   11040 tgcttcctca gccctagagg cgagccaggc aaggttggcg actgtcatgt ggcttggttt  11100
ggtcatgccc gtcgatgttt tgggtattga atgtggtaag tggaggaaat gttgaactc   11160 tgtgcaggtg ctgccttgag acccccaagc ttccacctgt ccctctccta tgtggcagct  11220
ggggagcagc tgagatgtgg acttgtatgc tgcccacata cgtgaggggg agctgaaagg  11280
gagcccctcc tctgagcagc ctctgccagg cctgtatgag gcttttccca ccagctccca  11340
acagaggcct cccccagcca ggaccacctc gtcctcgtgg cggggcagca ggagcggtag  11400
aaaggggtcc gatgtttgag gaggcccctta agggaagcta ctgaattata acacgtaaga  11460
aaatcaccat tccgtattgg ttgggggctc ctgtttctca tcctagcttt ttcctggaaa  11520
gcccgctaga aggtttggga acgaggggaa agttctcaga actgttggct gctccccacc  11580
cgcctcccgc ctccccgca ggttatgtca gcagctctga gacagcagta tcacaggcca   11640
gatgttgttc ctggctagat gtttacattt gtaagaaata acactgtgaa tgtaaaacag  11700
agccattccc ttggaatgca tatcgctggg ctcaacatag agtttgtctt cctcttgttt  11760
acgacgtgat ctaaaccagt ccttagcaag gggctcagaa caccccgctc tggcagtagg  11820
tgtcccccac cccaaagac ctgcctgtgt gctccggaga tgaatatgag ctcattagta   11880
aaaatgactt cacccacgca tatacataaa gtatccatgc atgtgcatat agacacatct  11940
ataattttac acacacacct ctcaagacgg agatgcatgg cctctaagag tgcccgtgtc  12000
ggttcttcct ggaagttgac tttccttaga cccgccaggt caagttagcc gcgtgacgga  12060
catccaggcg tgggacgtgg tcagggcagg gctcattcat tgcccactag gatcccactg  12120
gcgaagatgg tctccatatc agctctctgc agaaggagg aagactttat catgttccta   12180
aaaatctgtg gcaagcaccc atcgtattat ccaaattttg ttgcaaatgt gattaatttg  12240
```

```
gttgtcaagt tttggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaacccct ccagacaccc agaatgtagc atctgagaag    12540
gccctgtgcc ctaaaggaca cccctcgccc ccatcttcat ggagggggtc atttcagagc    12600
cctcggagcc aatgaacagc tcctcctctt ggagctgaga tgagcccac gtggagctcg    12660 ggacggatag tagacagcaa taactcggtg tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tccccgcttt    12840
cctccctctg cggggaggac ccgggaccac agctgctggc cagggtagac ttggagctgt    12900
cctccagagg ggtcacgtgt aggagtgaga agaaggaaga tcttgagagc tgctgaggga    12960
ccttggagag ctcaggatgg ctcagacgag acactcgct tgccgggcct gggcctcctg    13020
ggaaggaggg agctgctcag aatgccgcat gacaactgaa ggcaacctgg aaggttcagg    13080
ggccgctctt cccccatgtg cctgtcacgc tctggtgcag tcaaaggaac gccttcccct    13140
cagttgtttc taagagcaga gtctcccgct gcaatctggg tggtaactgc agccttgga    13200 ggatcgtggc caacgtggac ctgcctacgg agggtgggct ctgacccaag tggggcctcc    13260
ttgtccaggt ctcactgctt tgcaccgtgg tcagaggac tgtcagctga gcttgagctc    13320
ccctggagcc agcagggctg tgatgggcga gtcccggagc cccacccaga cctgaatgct    13380
tctgagagca aagggaagga ctgacgagag atgtatattt aatttttaa ctgctgcaaa    13440 cattgtacat ccaaattaaa ggaaaaaaat ggaaaccatc a                        13481
```

<210> SEQ ID NO 12
<211> LENGTH: 47
<212> TYPE: DNA
<213> ORGANISM: Artificial
<220> FEATURE:
<223> OTHER INFORMATION: shRNA molecule

<400> SEQUENCE: 12

```
aagaactttc agctaccaat ctcttgaatt ggtagctgaa agttctt                  47
```

<210> SEQ ID NO 13
<211> LENGTH: 86
<212> TYPE: DNA
<213> ORGANISM: Artificial
<220> FEATURE:
<223> OTHER INFORMATION: siGFP oligonucleotide

<400> SEQUENCE: 13

```
ctagtttcca aaaaagctg accctgaagt tcatctcttg aatgaacttc agggtcagct    60
tggggatctg tggtctcata cagaac                                         86
```

<210> SEQ ID NO 14
<211> LENGTH: 86
<212> TYPE: DNA
<213> ORGANISM: Artificial
<220> FEATURE:
<223> OTHER INFORMATION: sihtt1.1 oligonucleotide

<400> SEQUENCE: 14

```
ctagtttcca aaaaagaac tttcagctac caatctcttg aattggtagc tgaaagttct    60
```

```
tggggatctg tggtctcata cagaac                                           86
```

<210> SEQ ID NO 15
<211> LENGTH: 86
<212> TYPE: DNA
<213> ORGANISM: Artificial
<220> FEATURE:
<223> OTHER INFORMATION: sihtt3 oligonucleotide

<400> SEQUENCE: 15

```
ctagtttcca aaaagaccg tgtgaatcat tgttctcttg aaacaatgat tcacacggtc       60
tggggatctg tggtctcata cagaac                                           86
```

<210> SEQ ID NO 16
<211> LENGTH: 86
<212> TYPE: DNA
<213> ORGANISM: Artificial
<220> FEATURE:
<223> OTHER INFORMATION: sihtt6 oligonucleotide

<400> SEQUENCE: 16

```
ctagtttcca aaaagctttt gatggattct aattctcttg aaattagaat ccatcaaagc      60
tggggatctg tggtctcata cagaac                                           86
```

<210> SEQ ID NO 17
<211> LENGTH: 86
<212> TYPE: DNA
<213> ORGANISM: Artificial
<220> FEATURE:
<223> OTHER INFORMATION: sihtt13 oligonucleotide

<400> SEQUENCE: 17

```
ctagtttcca aaagcagct tgtccaggtt tattctcttg aaataaacct ggacaagctg       60
cggggatctg tggtctcata cagaac                                           86
```

<210> SEQ ID NO 18
<211> LENGTH: 26
<212> TYPE: DNA
<213> ORGANISM: Artificial
<220> FEATURE:
<223> OTHER INFORMATION: H1-3F primer

<400> SEQUENCE: 18

```
caccgaacgc tgacgtcatc aacccg                                           26
```

<210> SEQ ID NO 19
<211> LENGTH: 25
<212> TYPE: DNA
<213> ORGANISM: Artificial
<220> FEATURE:
<223> OTHER INFORMATION: tTRK-1F oligonucleotide

<400> SEQUENCE: 19

```
caccatgtct agattagata aaagt                                            25
```

<210> SEQ ID NO 20
<211> LENGTH: 22
<212> TYPE: DNA
<213> ORGANISM: Artificial
<220> FEATURE:
<223> OTHER INFORMATION: tTRK-2R oligonucleotide

<400> SEQUENCE: 20

```
ggatccttaa actgatgatt tg                                               22
```

<210> SEQ ID NO 21
<211> LENGTH: 22
<212> TYPE: DNA
<213> ORGANISM: Artificial
<220> FEATURE:
<223> OTHER INFORMATION: htt-3F forward primer

<400> SEQUENCE: 21
tgccagcact caagaaggac ac                                              22

<210> SEQ ID NO 22
<211> LENGTH: 23
<212> TYPE: DNA
<213> ORGANISM: Artificial
<220> FEATURE:
<223> OTHER INFORMATION: htt-2R reverse primer

<400> SEQUENCE: 22
cacgccaaga atcagcagag tgg                                             23

<210> SEQ ID NO 23
<211> LENGTH: 22
<212> TYPE: DNA
<213> ORGANISM: Artificial
<220> FEATURE:
<223> OTHER INFORMATION: BACTIN-1F primer

<400> SEQUENCE: 23
tgaaggtgac agcagtcggt tg                                              22

<210> SEQ ID NO 24
<211> LENGTH: 22
<212> TYPE: DNA
<213> ORGANISM: Artificial
<220> FEATURE:
<223> OTHER INFORMATION: BACTIN-2R primer

<400> SEQUENCE: 24
ggcttttagg atggcaaggg ac                                              22

<210> SEQ ID NO 25
<211> LENGTH: 22
<212> TYPE: DNA
<213> ORGANISM: Artificial
<220> FEATURE:
<223> OTHER INFORMATION: LACZ1F oligo

<400> SEQUENCE: 25
ccttactgcc gcctgttttg ac                                              22

<210> SEQ ID NO 26
<211> LENGTH: 22
<212> TYPE: DNA
<213> ORGANISM: Artificial
<220> FEATURE:
<223> OTHER INFORMATION: LACZ-2R oligo

<400> SEQUENCE: 26
tgatgttgaa ctggaagtcg cc                                              22

<210> SEQ ID NO 27
<211> LENGTH: 20
<212> TYPE: DNA
<213> ORGANISM: artificial sequence
<220> FEATURE:
<223> OTHER INFORMATION: htt C primer

```
<400> SEQUENCE: 27
ggggtgacac ggaaagaaat                                               20

<210> SEQ ID NO 28
<211> LENGTH: 20
<212> TYPE: DNA
<213> ORGANISM: artificial sequence
<220> FEATURE:
<223> OTHER INFORMATION: htt D primer

<400> SEQUENCE: 28
tcagtgcttg caggagttca                                               20

<210> SEQ ID NO 29
<211> LENGTH: 20
<212> TYPE: DNA
<213> ORGANISM: artificial sequence
<220> FEATURE:
<223> OTHER INFORMATION: CYCLO-1F primer

<400> SEQUENCE: 29
atggcaaatg ctggaccaaa                                               20

<210> SEQ ID NO 30
<211> LENGTH: 21
<212> TYPE: DNA
<213> ORGANISM: artificial sequence
<220> FEATURE:
<223> OTHER INFORMATION: CYCLO-2R primer

<400> SEQUENCE: 30
gccttctttc accttcccaa a                                             21
```